US009546364B2

(12) United States Patent
Das et al.

(10) Patent No.: US 9,546,364 B2
(45) Date of Patent: Jan. 17, 2017

(54) SYNTHETIC LARIAT RNA FOR RNA INTERFERENCE

(71) Applicant: Carnegie Mellon University, Pittsburgh, PA (US)

(72) Inventors: Subha Ranjan Das, Pittsburgh, PA (US); Eduardo Paredes, Cincinnati, OH (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 14/213,164

(22) Filed: Mar. 14, 2014

(65) Prior Publication Data

US 2014/0273216 A1 Sep. 18, 2014

Related U.S. Application Data

(60) Provisional application No. 61/852,250, filed on Mar. 15, 2013.

(51) Int. Cl.
 *C12N 15/113* (2010.01)
 *C12N 15/11* (2006.01)

(52) U.S. Cl.
 CPC ....... *C12N 15/111* (2013.01); *C12N 2310/319* (2013.01)

(58) Field of Classification Search
 USPC ............. 435/6.1, 91.1, 91.31; 536/23.1, 24.5
 See application file for complete search history.

(56) References Cited

U.S. PATENT DOCUMENTS

| | | | |
|---|---|---|---|
| 8,546,143 B2 | 10/2013 | Kreutzer et al. | |
| 8,563,710 B2 | 10/2013 | Liang | |
| 8,580,754 B2 | 11/2013 | Fire et al. | |
| 8,637,482 B2 | 1/2014 | Feinstein et al. | |
| 8,658,356 B2 | 2/2014 | Rossi et al. | |
| 2011/0229880 A1* | 9/2011 | Wood | C12N 15/111 435/6.1 |
| 2011/0245329 A1* | 10/2011 | Pachuk | A61K 48/00 514/44 R |
| 2013/0046084 A1* | 2/2013 | Brown | C07H 1/00 536/23.1 |

OTHER PUBLICATIONS

Mitra et al, J. Org. Chem., vol. 72, pp. 9491-9500 (2007).*
Carriero et al, J. Org. Chem, vol. 68, pp. 8328-8338 (2003).*
Carriero et al, Curr. Protocols in Nucl. Acid. Chem., vol. 4.14.1-4.14.32 (2002).*
Averick et al., "Autotransfecting Short Interfering RNA through Facile Covalent Polymer Escorts", J. Am. Chem. Soc., 2013, pp. 12508-12511, vol. 135.
Bartel, "MicroRNAs: Genomics, Biogenesis, Mechanism, and Function", Cell, 2004, pp. 281-297, vol. 116.
Beaucage, "Solid-phase synthesis of siRNA oligonucleotides", Current Opinion in Drug Discovery & Development, 2008, pp. 203-216, vol. 11, No. 2.
Bernstein et al., "Role for a bidentate ribonuclease in the initiation step of RNA interference", Nature, 2001, vol. 209.
Beringer, Remington: The Science and Practice of Pharmacy, 2005, Chapters 37, 39, 41, 42, 45, 50, and 65, 21st Edition.
Bosse et al., "A new twist in the microRNA pathway: Not Dicer but Argonaute is required for a MicroRNA production", Cell Research, 2010, pp. 735-737, vol. 20.
Carriero et al., "Solid-Phase Synthesis of Branched Oligonucleotides", Current Protocols in Nucleic Acid Chemistry, 2002, pp. 4.14.1-4.14.32, vol. 4.
Carriero et al., "Template-Mediated Synthesis of Lariat RNA and DNA", J. Org. Chem., 2003, pp. 8328-8338, vol. 68.
Chakravarthy et al., "Substrate-specific kinetics of Dicer-catalyzed RNA Processing" J Mol Biol., 2010, pp. 392-402, vol. 404, No. 3.
Chapman et al., "Isolation and Characterization of the Gene Encoding Yeast Debranching Enzyme", Cell, 1991, pp. 483-492, vol. 65.
Cheloufi, "A Dicer-independent miRNA biogenesis pathway that requires Ago catalysis", Nature, 2010, pp. 584-589, vol. 465, No. 7298.
Chen et al., "Progress on RNAi-based molecular medicines", International Journal of Nanomedicine, 2012, pp. 3971-3980, vol. 7.
Chendrimada et al., "TRBP recruits the Dicer complex to Ago2 for microRNA processing and gene silencing", Nature, 2005, pp. 740-744, vol. 436, No. 7051.
Dey et al., "The Diverse Active Sites in Splicing, Debranching, and MicroRNA Processing Around RNA Phosphodiester Bonds", From Nucleic Acids Sequences to Molecular Medicine, 2012, pp. 475-501.
Elkayam et al., "The Structure of Human Argonaute-2 in Complex with miR-20a", Cell., 2012, pp. 100-110, vol. 150, No. 1.
Fire et al., "Potent and specific genetic interference by double-strand RNA in Caenorhabditis elegans" Nature, 1998, pp. 806-811, vol. 391.
Gaglione et al., "Recent Progress in Chemically Modified siRNAs" Mini-Reivews in Medicinal Chemistry, 2010, pp. 578-595, vol. 10.
Gaynor et al., "RNA interference: a chemist's perspective", Chem. Soc. Rev., 2010, pp. 4169-4184, vol. 39.
Hammond, "Dicing and slicing the core machinery of the RNA interference pathway", FEBS Letters, 2005, pp. 5822-5829, vol. 579.
Ketting, "The Many Faces of RNAi", Developmental Cell, 2011, pp. 148-161, vol. 20.
Kim et al., "Human RNA lariat debranching enzyme cDNA complements the phenotypes of *Saccharomyces cerevisiae* dbr1 and *Schizosaccharomyces pombe* dbr1 mutants", Nucleic Acids Research, 2000, pp. 3666-3673, vol. 28, No. 18.
Kim et al., "Synthetic dsRNA Dicer substrates enhance RNAi potency and efficacy" Nature Biotechnology, 2005, pp. 222-226, vol. 23, No. 2.
Kim "MicroRNA Biogenesis: Coordinated Cropping and Dicing" Nature Reviews: Molecular Cell Biology, 2005, pp. 376-385, vol. 6.
Kole et al., "RNA therapeutics: beyond RNA interference and antisense oligonucleotides" Nature Reviews Drug Discovery, 2012, pp. 125-140, vol. 11.
Kubo et al., "Amino-Modified and Lipid-Conjugated Dicer-Substrate siRNA Enhances RNAi Efficacy", Bioconjugate Chemistry, 2012, pp. 164-173, vol. 23.

(Continued)

*Primary Examiner* — Jane Zara
(74) *Attorney, Agent, or Firm* — The Webb Law Firm

(57) ABSTRACT

Provided herein are compositions for the modification of gene expression by RNA interference using a microRNA (miRNA) guide strand precursor. Methods of making and using the miRNA guide strand precursor also are provided. The compositions bypass the Drosha-Exportin-Dicer pathway and are resistant to nucleases.

16 Claims, 16 Drawing Sheets

(56) References Cited

OTHER PUBLICATIONS

Kwak et al., "The microRNA pathway and cancer", Cancer Science, 2010, pp. 2309-2315, vol. 101, No. 11.
Ladewig et al., "Discovery of hundreds of mirtrons in mouse and human small RNA data", Genome Research, 2012, pp. 1634-1645, vol. 22.
Lee et al., "The nuclear RNase III Drosha initiates microRNA processing", Nature, pp. 415-419, 2003, vol. 425.
Lewis et al., "Discovery and Characterization of Catalysts for Azide-Alkyne Cycloaddition by Fluorescence Quenching", J. Am. Chem. Soc., 2004, pp. 9152-9153, vol. 126.
Lima et al., "Single-Stranded siRNAs Activate RNAi in Animals", Cell, 2012, 883-894, vol. 150.
Lin et al., "Intronic MicroRNA (miRNA)", Journal of Biomedicine and Biotechnology, 2006, pp. 1-13.
Miller et al., "Versatile 5'-Functionalization of Oligonucleotides on Solid Support: Amines, Azides, Thiols, and Thioethers via Phosphorus Chemistry", J. Org. Chem., 2004, pp. 2404-2410, vol. 69.
Mitra et al., "A Novel Approach to the Synthesis of DNA and RNA Lariats" J. Org. Chem., 2007, pp. 9491-9500, vol. 72.
Mulcahy et al., "RNAi2013: RNAi at Oxford" Journal of RNAi and Gene Silencing, 2013, pp. 486-489, vol. 9.
Nam et al., "Yeast Lariat Debranching Enzyme", The Journal of Biological Chemistry, 1994, pp. 20613-20621, vol. 269, No. 32.
Nam et al., "Severe Growth Defect in a Schizosaccharomyces pombe Mutant Defective in Intron Lariat Degradation", Molecular and Cellular Biology, 1997, pp. 809-818, vol. 17, No. 2.
Ohrt et al., "siRNA Modifications and Sub-Cellular Localization: A Question of Intracellular Transport?", Current Pharmaceutical Design, 2008, pp. 3674-3685, vol. 14.
Okamura et al., "The Mirtron Pathway Generates microRNA-Class Regulatory RNAs in *Drosophila*", Cell, 2007, pp. 89-100, vol. 130, No. 1.
Ooi et al., "RNA Lariat Debranching Enzyme", Methods in Enzymology, 1984, pp. 233-248, vol. 342.
Paredes et al., "Click Chemistry for Rapid Labeling and Ligation of RNA" ChemBioChem, 2011, pp. 125-131, vol. 12.
Ruby et al., "Intronic microRNA precursors that bypass Drosha processing", Nature, 2007, pp. 83-86, vol. 448, No. 7149.
Ruskin et al., "An RNA Processing Activity That Debranches RNA Lariats", Science, 1985, pp. 135-140, vol. 229.
Shen et al., "Delivery of gene silencing agents for breast cancer therapy", Breast Cancer Research, 2013, pp. 1-8, vol. 15, No. 205.
Shruti et al., "Micro RNAs: Tiny sequences with enormous potential", Biochemical and Biophysical Research Communications, 2011, pp. 445-449, vol. 407.
Shukla, "Exploring Chemical Modifications for siRNA Therapeutics: A Structural and Functional Outlook", ChemMedChem, 2010, pp. 328-349, vol. 5.
Sikand et al., "miR 488* inhibits androgen receptor expression in prostate carcinoma cells", Int J Cancer, 2011, pp. 1-19, vol. 129, No. 4.
Slezak-Prochazka et al., "MicroRNAs, macrocontrol: Regulation of miRNA processing" RNA, 2010, pp. 1087-1095, vol. 16.
Wang et al., "A general two-step strategy to synthesize lariat RNAs", RNA, 2006, pp. 313-321, vol. 12.
Wang et al., "Deoxyribozymes that Synthesize Branched and Lariat RNA", J. Am. Chem. Soc. 2003, pp. 6880-6881, vol. 125.
Yamada et al., "Versatile Site-Specific Conjugation of Small Molecules to siRNA Using Click Chemistry", J. Org. Chem., 2011, pp. 1198-1211, vol. 76.

\* cited by examiner

SEQUENCE LISTING

<160> NUMBER OF SEQ ID NOS: 11

<210> SEQ ID NO 1
<211> LENGTH: 56
<212> TYPE: RNA
<213> ORGANISM: Artificial Sequence
<220> FEATURE:
<223> OTHER INFORMATION: miR-1003 pre-miRNA

<400> SEQUENCE: 1
guggguaucu ggauguggu ggcucuggcg guccucucac auuuacauau ucacag            56

<210> SEQ ID NO 2
<211> LENGTH: 22
<212> TYPE: RNA
<213> ORGANISM: Artificial Sequence
<220> FEATURE:
<223> OTHER INFORMATION: mir-1003 guide strand

<400> SEQUENCE: 2
ucucacauuu acauauucac cc                                                22

```
<210> SEQ ID NO 3
<211> LENGTH: 21
<212> TYPE: DNA
<213> ORGANISM: Artificial Sequence
<220> FEATURE:
<223> OTHER INFORMATION: anti-luciferase guide strand

<400> SEQUENCE: 3
uugauuaacg cccagcguut t                                              21

<210> SEQ ID NO 4
<211> LENGTH: 18
<212> TYPE: RNA
<213> ORGANISM: Artificial Sequence
<220> FEATURE:
<223> OTHER INFORMATION: miR664a

<400> SEQUENCE: 4
aguguggcuu ucuuagag                                                  18

<210> SEQ ID NO 5
<211> LENGTH: 58
<212> TYPE: RNA
<213> ORGANISM: Artificial Sequence
<220> FEATURE:
<223> OTHER INFORMATION: Let-7

<400> SEQUENCE: 5
augagguagu agguuguaua guuuuagggu cacaccccua uacaaucuac ugucuuuc      58

<210> SEQ ID NO 6
<211> LENGTH: 23
<212> TYPE: RNA
<213> ORGANISM: Artificial Sequence
<220> FEATURE:
<223> OTHER INFORMATION: Mir17

<400> SEQUENCE: 6
caaagugcuu acagugcagg uag                                            23

<210> SEQ ID NO 7
<211> LENGTH: 20
<212> TYPE: DNA
<213> ORGANISM: Artificial Sequence
<220> FEATURE:
<223> OTHER INFORMATION: DNA splint for ligation

<400> SEQUENCE: 7
aaccacatcc agatacccac                                                20

<210> SEQ ID NO 8
<211> LENGTH: 20
<212> TYPE: DNA
<213> ORGANISM: Artificial Sequence
<220> FEATURE:
<223> OTHER INFORMATION: DNA splint for ligation

<400> SEQUENCE: 8
tgtaaatgca cccatagacc                                                20

<210> SEQ ID NO 9
<211> LENGTH: 56
<212> TYPE: RNA
<213> ORGANISM: Artificial Sequence
<220> FEATURE:
<223> OTHER INFORMATION: RNA3
```

```
<400> SEQUENCE: 9
gugggUaucu ggaugugguu ggcucuggcg guccucucac auuuacauau ucacag        56

<210> SEQ ID NO 10
<211> LENGTH: 21
<212> TYPE: RNA
<213> ORGANISM: Artificial Sequence
<220> FEATURE:
<223> OTHER INFORMATION: RNA4

<400> SEQUENCE: 10
cucacauuua cauauucaca g                                              21

<210> SEQ ID NO 11
<211> LENGTH: 20
<212> TYPE: RNA
<213> ORGANISM: Artificial Sequence
<220> FEATURE:
<223> OTHER INFORMATION: RNA5

<400> SEQUENCE: 11
gugggUaucu ggaugugguu                                                20
```

US 9,546,364 B2

SYNTHETIC LARIAT RNA FOR RNA INTERFERENCE

CROSS REFERENCE TO RELATED APPLICATIONS

This application claims the benefit of U.S. Provisional Patent Application No. 61/852,250, filed Mar. 15, 2013, which is incorporated herein by reference in its entirety.

SEQUENCE STATEMENT

The Sequence Listing associated with this application is filed in electronic format via EFS-Web and is hereby incorporated by reference into the specification in its entirety. The name of the text file containing the Sequence Listing is 140659_ST25.txt. The size of the text file is 2,319 bytes, and the text file was created on Mar. 14, 2014.

BACKGROUND OF THE INVENTION

Field of the Invention

Compositions and methods are provided for modifying the expression of genes. More particularly, synthetic RNA structures for silencing genes through RNA interference (RNAi), and methods of using those synthetic structures for silencing genes of interest are provided.

Description of Related Art

RNA interference (RNAi) is the process of post-transcriptional repression of a target gene by small non-coding RNAs. The biogenesis of these small microRNAs from long primary transcripts yields RNAs which are loaded on to the RNA-induced silencing complex (RISC), which can bind to target RNA and catalyze its endonucleolytic cleavage thereby turning over the target transcript for degradation. The process of inducing RNAi with synthetic short-interfering RNAs (siRNAs) is traditionally initiated by delivery of precursor RNAs which are further processed by the enzyme Dicer, an endonuclease in the RNAi pathway, and then the resulting RNA strand, typically 20-25 residues long, is loaded into RISC.

The two main drawbacks to this standard approach are the significant RNA degradation observed over time in serum and the significant challenges of delivery. To address the stability issues, modified duplexes of the siRNAs which exhibit nuclease resistance and potent RNAi activity are introduced into cells. However, therapeutic delivery of these larger RNA constructs is challenging.

Mature miRNAs are short RNAs which can be easily synthesized in the solid-phase and thus researchers have used small synthetic RNAs to induce an RNAi response. These small-interfering RNAs (siRNAs) are generally delivered as duplexes and exhibit powerful gene interference. The main drawback of the use of siRNAs in RNAi is that without a steady source of the siRNAs, the transfected RNAs quickly succumb to cellular RNases and thus their effect is generally short-lived. This has driven researchers to develop modifications to these siRNAs that both lengthen the interference effect and improve their potency. The types of modifications range from backbone modifications that provide RNase stability, sugar modifications to improve siRNA binding and RNAse stability and base modifications to provide increased affinity and target selectivity. Additionally, the use of siRNA mimics, siRNA conjugates or delivery vehicles has been reported to induce powerful RNAi responses. However the use of some modifications, including phosphorothioates, 2'-OMe or 2'-fluoro, can lead to undesired side-reactions or affected pharmacokinetic properties.

Recent reports suggest that most miRNAs derive from non-coding regions of genes, with nearly eighty percent of mouse and human miRNAs originating in introns of mRNA-coding genes. These mirtron sequences are located as isolated sequences flanked by exons, and thus require efficient splicing for their excision from the main transcript sequence. The highly conserved splice site residues, once spliced and debranched by debranching enzyme (Dbr), generate a hairpin similar to that generated by Drosha. Therefore, these pre-miRNA transcripts require Dbr activity but do not require Drosha activity for maturation. Following Dbr debranching, mirtron-derived pre-miRNAs are exported and processed like canonical miRNAs. However, these alterations to the traditional miRNA pathway do not address several issues, such as duration of the effect.

SUMMARY OF THE INVENTION

Accordingly, to address the need for longer-lasting siRNAs capable of long-term silencing of genes of interest without the concomitant side-effects, a need exists in the art for compositions having a longer siRNA lifetime that are advantageous for methods of RNAi therapy. These compositions include miRNAs having lariat structures, that are protected from cellular nucleases/RNases and that avoid the Drosha-Exportin-Dicer processing pathway and that, following debranching by Dbr, induce an RNAi response.

A method of knocking down expression of a gene in a eukaryotic cell is provided. The method comprises introducing into the cell a micro RNA (miRNA) guide strand precursor having a sequence at least partially complementary to a mRNA produced by the gene and having a lariat structure, in an amount effective to reduce expression of the gene, the miRNA guide strand precursor having an oligonucleotide sequence of from 20 to 25 residues and having a 5' end and a 3' end. To form the lariat structure, the 5' end is attached to a 2' position of a residue at least five residues from the 5' end and at least one residue from the 3' end of the oligonucleotide sequence to form a lariat structure comprising a loop portion. According to one embodiment, the loop portion comprises a triazole linkage at one 5' to 3' linkage between two residues. In certain embodiments, the oligonucleotide sequence is 20, 21, 22, 23, 24 or 25 residues. In one embodiment, the loop portion consists of between 5 and 20 residues, including integers therebetween, for example 15 residues. In one embodiment, the 3' end of the oligonucleotide is protected, for example, by one, two or more 2' deoxyribonucleotides incorporated into the oligonucleotide at its 3' end. In one embodiment, the miRNA guide strand is introduced into the cell by contacting the cell with the liposome containing the branched miRNA guide strand.

In another embodiment, a solid-phase method of preparing an miRNA guide strand precursor having a lariat structure is provided. The method comprising preparing on a solid support a lariat structure having a miRNA sequence that is at least partially complementary to a target mRNA: adding at least two nucleotide residues to the solid support in a 3' to 5' direction; adding residues to the 5' and 2' positions of the 5' terminal residue, producing a 5' strand and a 2' strand; terminating the 5' strand with a terminal residue having either a 5' alkyne group or a 5' azide group; terminating the 2' strand with a terminal residue having a 3' terminal alkyne when the terminal residue of the 5' strand has a 5' azide group or a 3' azide group when the terminal residue of the 5' strand has a 5' alkyne group; ligating the 5' terminal alkyne or azide of the terminal residue of the 5' strand with the 3'-terminal azide or alkyne, respectively, of the terminal residue of the 2' strand to produce a triazole linkage between the terminal residue of the 5' strand and the terminal residue of the 2' strand; and deprotecting the lariat structure and cleaving the structure from the solid support, wherein the total number of nucleotide residues in the miRNA guide strand precursor is between 20 and 25 residues and has a sequence that is at least partially complementary to an mRNA, thereby producing a miRNA guide strand precursor. In one embodiment, the 3'-terminal residue of the 2' strand is a 2'-3'-dideoxy-3'-O-propargyl-adenosine residue that contains the 3'-terminal alkyne (propargyl group). Another embodiment, comprises protecting the 3' end of the structure from RNAse degradation, for example by adding one or more 2'-deoxyribonucleotide residues to the 3' end of the structure to protect the structure from RNAse degradation. To prepare a deliverable composition, according to one embodiment, the method comprises incorporating the synthetic nucleic acid lariat into a delivery vehicle, such as a liposome. As above, in one embodiment, the nucleic acid lariat comprises 20, 21, 22, 23, 24 or 25 residues. In another embodiment, the loop portion includes between 5 and 20 nucleotides, for example 15 nucleotides.

In another embodiment, a method of forming a synthetic nucleic acid lariat is provided. The method comprising: synthesizing an oligonucleotide, incorporating a phosphoramidite group at the 5' end of the oligonucleotide and incorporating a 2'-photoprotected group in the oligonucleotide between the 5' end and the 3' end; unmasking the 2'-photoprotected group to provide a 2'-hydroxyl; and activating the 5'-phosphoramidite and linking the 5' end of the oligonucleotide to the 2'-hydroxyl to form a phosphodiester-linked synthetic nucleic acid lariat. In one embodiment, the oligonucleotide is an RNA oligonucleotide. As above, in one embodiment, the nucleic acid lariat comprises 22 nucleotides. In another embodiment, the loop portion is between 5 and 20 nucleotides in length, for example, 15 nucleotides. In one embodiment, the 2'-photoprotected group is a 2'-O-photoprotected amidite.

In yet another embodiment, a synthetic micro RNA (miRNA) guide strand precursor having a sequence at least partially complementary to an RNA produced by a gene and having a lariat structure is provided. The miRNA guide strand precursor has an oligonucleotide sequence of from 20 to 25 residues and has a 5' end and a 3' end. The 5' end is attached to a 2' position of a residue at least five residues from the 5' end and at least one residue from the 3' end of the oligonucleotide to form a lariat structure comprising a loop portion. In one embodiment, the loop portion comprises at one 5' to 3' linkage between two residues a triazole linkage. In another embodiment, the oligonucleotide comprises ribonucleotide residues. In one embodiment, the oligonucleotide is 22 nucleotides in length. In another embodiment, the looped portion is between 5 and 20 nucleotides in length, for example, 15 nucleotides. In another embodiment, the 3' end of the oligonucleotide is protected, for example by the addition of a 2'-deoxyribonucleotide residue at the 3' end of the oligonucleotide.

DESCRIPTION OF THE INVENTION

Figure 1:
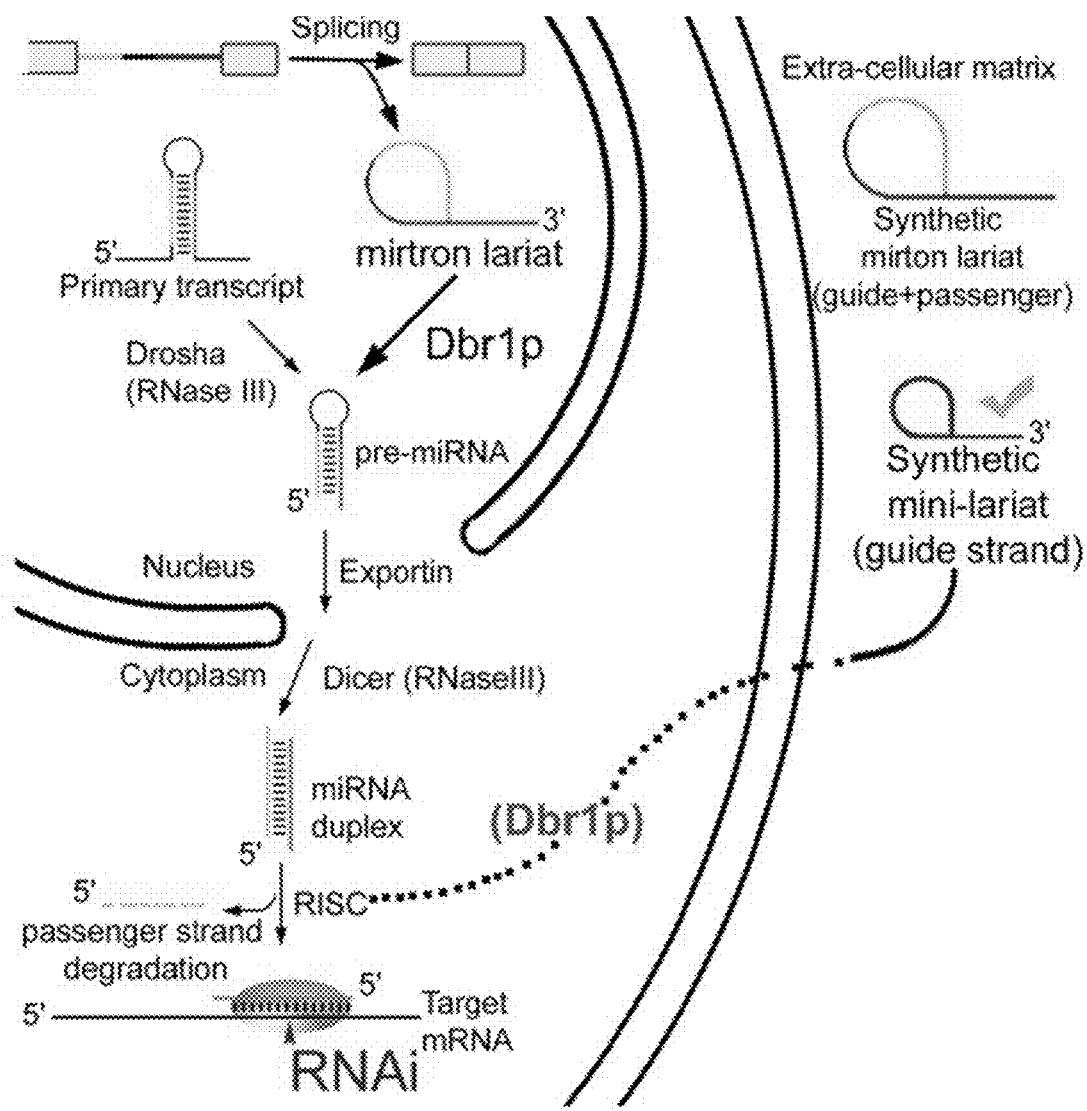
FIG. 1 shows a schematic of the micro RNA (miRNA) and mirtron processing pathways in the nucleus, and the pathway of the compositions of one embodiment of the present invention.

Provided herein are compositions for the modification of gene expression through RNA interference, including knockdown and gene silencing, methods of producing the same, and methods of using the same to modify the expression of genes.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

By "expression" it is meant the overall flow of information from a gene (without limitation, a functional genetic unit for producing a gene product in a cell or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

As used herein, the term "knockdown" means that expression of one or more genes in an organism is reduced, typically significantly, with respect to a functional gene, such as to a therapeutically-effective degree. Gene knockdown may also include complete gene silencing. As used herein, "gene silencing" means that expression of a gene is essentially completely prevented. Knockdown and gene silencing may occur either at the transcriptional stage or the translational stage. Use of miRNA guide strand precursors as described herein modifies gene expression, by knocking down or silencing a gene or genes, at the translational stage.

As used herein, the term "nucleic acid" refers to deoxyribonucleic acids (DNA), ribonucleic acids (RNA), and analogues thereof (for example and without limitation 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, and threose nucleic acids), which are formed by strings of nucleotides. Herein, "nucleic acid" and "oligonucleotide", which is a short, single-stranded structure made of up nucleotides, are used interchangeably. An oligonucleotide may be referred to by the length (i.e. number of nucleotides) of the strand, through the nomenclature "-mer". For example, an oligonucleotide of 22 nucleotides would be referred to as a 22-mer.

As used herein the term "lariat" refers to a specific structure of an oligonucleotide that has three portions, a linear or substantially linear portion, a branch, and a loop portion. In a lariat, the loop portion may be the 5' end of the oligonucleotide ligated, bonded, or otherwise attached to an internal, branching nucleotide within the linear portion, though various modifications to the 5' end and the internal, branching nucleotide fall within the spirit and scope of the present invention. For example, and without limitation, various groups may be added to the internal, branching nucleotide for ligation to the 5' end, or one or more nucleotides may form a branch off of the internal, branching nucleotide and that branch may be ligated to the 5' end of the oligonucleotide. The oligonucleotide may be modified in any number of ways to aid in ligation and formation of the lariat structure. Ligation refers to the linking of two nucleotide strands, typically by a 3' to 5' linkage, but potentially through other linkages, such as a 2' to 5' linkage through, e.g., phosphodiester linkage

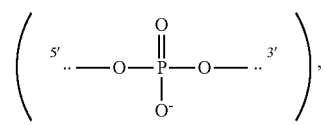

as is commonly found in natural RNA or DNA, or other linkages, such as the triazole linkage

Figure 3A:
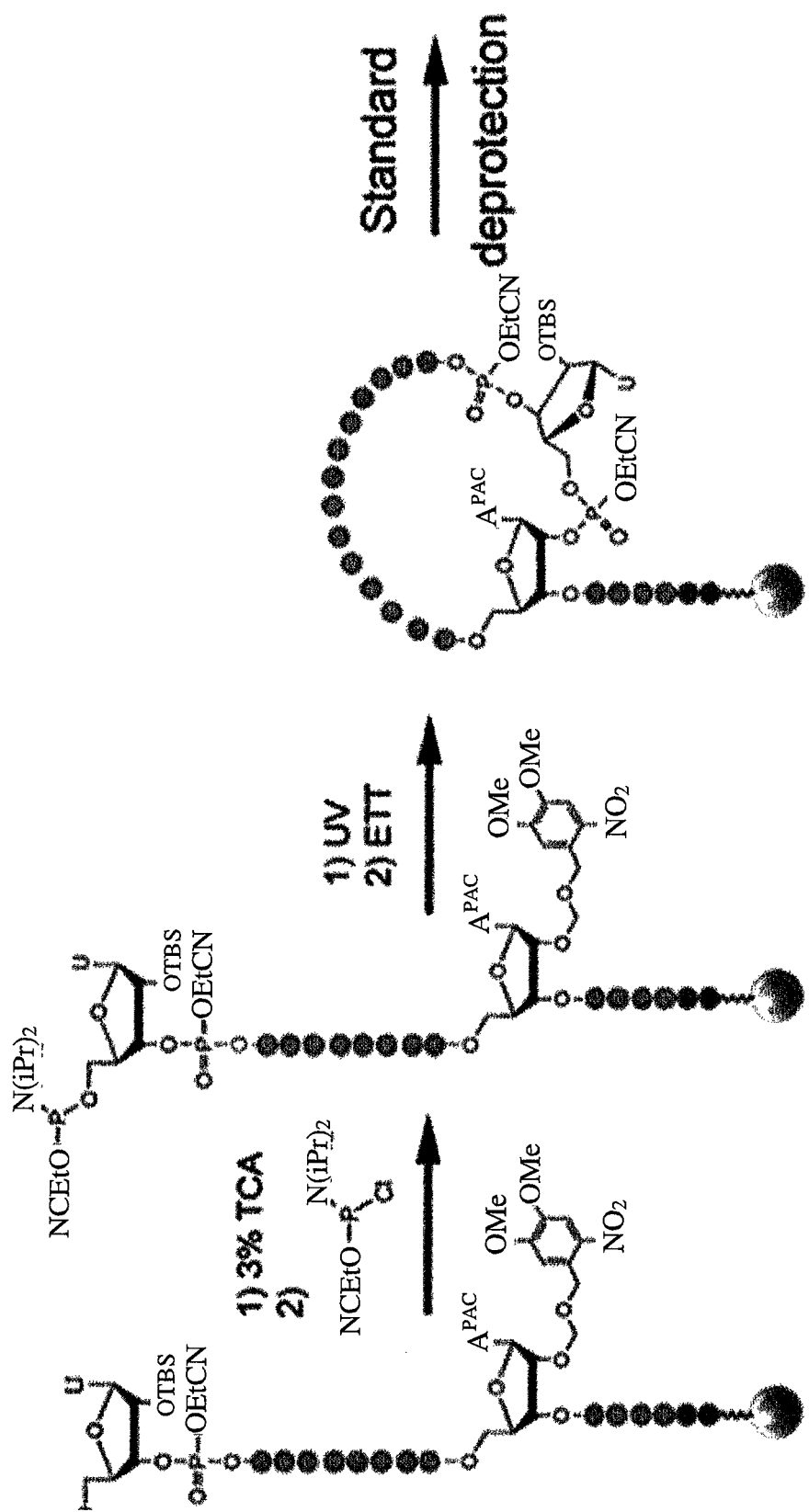
FIG. 3A-E shows solid-phase synthesis of lariat siRNAs for RNAi: A. Synthesis of click-linked lariat siRNA in the solid-phase. Following synthesis of the clickable backbone branched RNA6 precursor, a click ligation in the solid-phase yields the lariat RNA6; B. Following synthesis of RNA7 precursor, selective 5'-OH to phosphoramidite synthesis is carried out in two steps adapting reported methods. Following phosphoramidite synthesis, selective 2'-OH unmasking and further coupling, yields lariat RNA7. C. shows the sequence of the miR-1003 guide strand that is generated following debranching (SEQ ID NO: 2). Black pentagon denotes the triazole linkage in the click-linked lariat siRNA. Circled A denotes branch-point adenosine and the bracket denotes the miRNA seed sequence; D. Polyacrylamide gel (10%-8M Urea) used to resolve debranching reactions of RNA6,7 (800 pmol) with Dbr (25 pmol) in 50 mM Tris.HCl (pH 7.5), $MnCl_2$ (80 nmol), DTT (100 nmol), and NaCl (500 nmol) for 30 min at 30° C. The +/− lane denotes a co-loading of − and + reaction mixtures which confirms that the bands observed are two different RNA populations; E. Plots of RNAi activity against a luciferase reporter using RNA4 (circles and trace), RNA5 (squares and trace), siRNA duplex of RNA4,5 (upside down triangles and trace), RNA6 (hexagon and trace) and RNA7 (triangles and trace). The lariat siRNAs exhibit potent RNAi activity that persists to ~70% after 7 days.
Figure 3B:
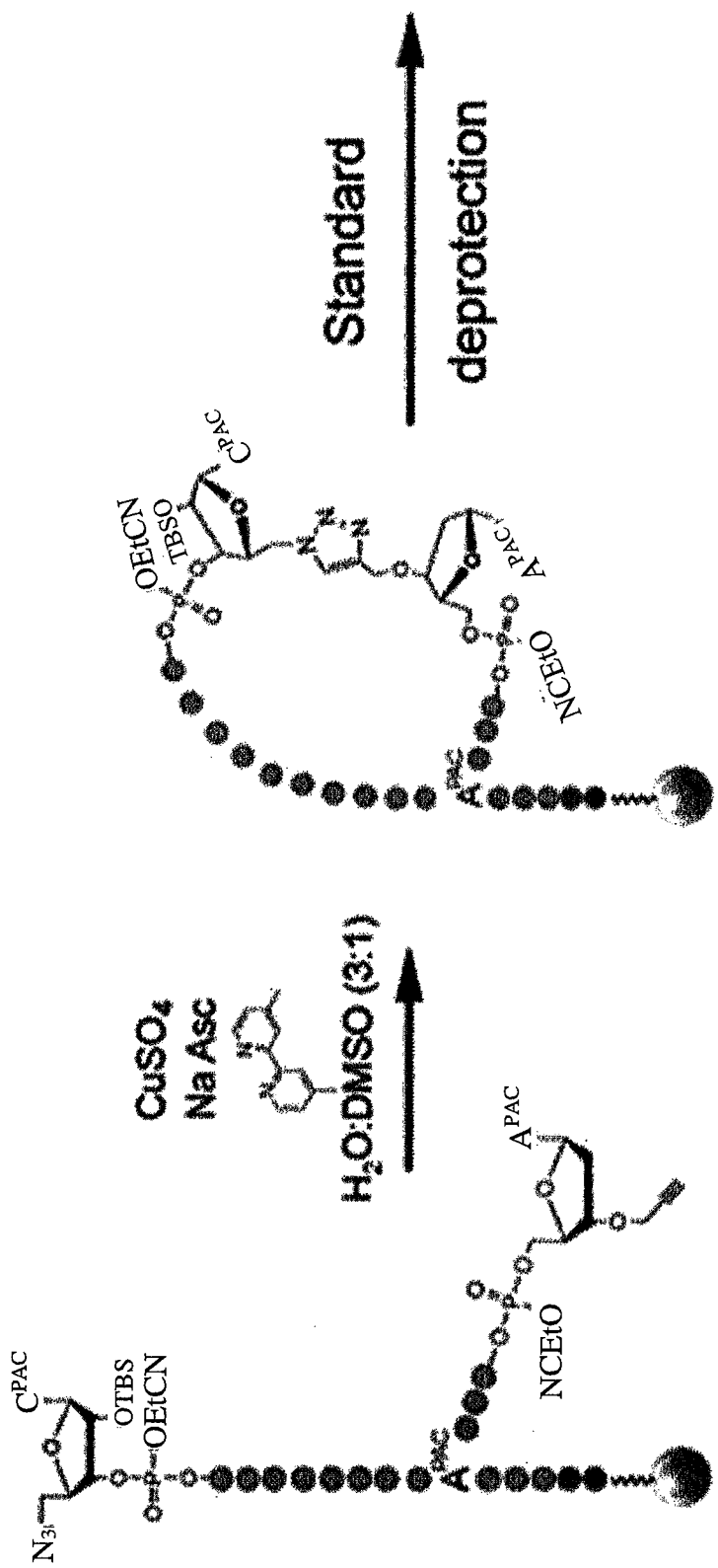

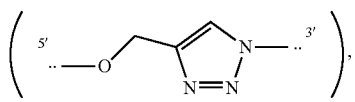

as shown in FIG. 3b (in both instances, the 3' and 5' indicate directionality in the nucleotide sequence and the depicted structures extend to, but do not include 3' and 5' carbon atoms of the adjacent ribonucleotides or deoxyribonucleotides). These nucleic acid lariat structures act as miRNA precursors and are effective in modifying gene expression. As used herein, the term "synthetic nucleic acid lariat" is used interchangeably with "nucleic acid lariat", and "lariat structure," and where appropriate, "click lariat" and "click-linked lariat". A "linkage" refers to the chemical moiety that acts as a connection between two adjacent nucleotide sugars (e.g., ribose or deoxyribose), for example the 3' to 5' phosphodiester linkage depicted above that is common to natural mRNA and DNA.

As used herein, the term "mirtron" means a short (micro) RNA (miRNA) structure within the intron (coding region) of a transcribed nucleic acid (mRNA) of a gene. Natively, mirtrons are miRNA precursors, which are present in the exon (non-coding region) of a gene, and function to modify gene expression, including the knockdown or silencing of genes. miRNA gene modification occurs through a well-known pathway (FIG. 1), that includes formation of a hairpin by a primary-miRNA (Pri-miRNA; transcribed from an exon of a gene), processing by Drosha to yield Pre-miRNA, and export from the nucleus via Exportin. Once in the cytoplasm, the Pre-miRNA is further processed by Dicer to provide mature miRNA, which through interaction with the RNA-induced silencing complex (RISC) can modify expression of a gene through binding to mRNA transcripts having at least a partial or substantially complementary sequence to the miRNA. For further background on the miRNA process, see Hammond et al. Dicing and Slicing: The Core Machinery of the RNA Interference Pathway. *FEBS Letters* 579(26): 5822-5829 (2005), particularly FIG. 3.

Mirtrons achieve similar effects to miRNA, but are able to do so differently, bypassing the Drosha pathway (FIG. 1), and thereby avoiding any "bottlenecking" that might occur in the non-mirtron miRNA pathway. Unlike miRNAs, mirtrons are found within introns within the coding regions of a gene and which, once excised from pre-mRNA, are substrates for debranching enzyme (Dbr), which modifies the mirtron to provide the pre-miRNA, with its hairpin structure. For further background on the mirtron pathway, see Ruby et al. Intronic microRNA precursors that bypass Drosha Processing. *Nature* 448(7149): 83-86 (2007).

Methods are provided for producing miRNA guide strand precursors that are capable of avoiding the Drosha-Exportin-Dicer pathways, along with any inherent bottlenecks or other shortcomings, and effectively modify gene expression for a significantly longer period of time than is possible via mirtrons (FIG. 1) or even knockdown with un-modified RISC guide strand ssRNA or dsRNA. The precursor includes a lariat structure that is debranched by Dbr to form a miRNA guide (active) strand that can be processed into RISC and that exhibits long-lasting effects on the target genes of interest (FIG. 1) due to its nuclease resistance. The miRNA precursors may be formed by any useful method of producing oligonucleotides, such as by solid-phase synthesis methods. Such standard synthesis reactions are well known to those of skill in the art, and may be accomplished using commercial devices and/or kits.

According to one non-limiting embodiment, a method of knocking down expression of a gene in a eukaryotic cell is provided. The method comprises introducing into the cell a micro RNA (miRNA) guide strand precursor having a sequence at least partially complementary to a mRNA produced by the gene and having a lariat structure, in an amount effective to reduce expression of the gene, the miRNA guide strand precursor comprising an oligonucleotide sequence of from 20 to 25 residues and having a 5' end and a 3' end, wherein the 5' end is attached to a 2' position of a residue at least five residues from the 5' end and at least one residue from the 3' end of the oligonucleotide to form a lariat structure comprising a loop portion. In one-non-limiting embodiment, the loop portion comprises at one 5' to 3' linkage between two residues either a phosphodiester linkage

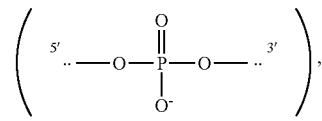

or a triazole linkage

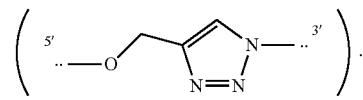

In one embodiment, the oligonucleotide is prepared by solid-phase synthesis. As used herein, "solid-phase synthesis" means that the nucleotides are bound on a solid phase, for example and without limitation a bead of controlled pore glass (CPG) or polystyrene (for example, and without limitation, macroporous polystyrene (MPPS)), and the oligonucleotide is synthesized step-by-step in a reactant solution using appropriate nucleosides (2'deoxynucleosides, ribonucleosides, or other chemically-modified nucleosides). As known to those of skill in the art, solid-phase synthesis proceeds most efficiently on a non-swellable solid support, or a support that is minimally swellable. Use of a solid-phase synthesis protocol allows for easier isolation of the resultant oligonucleotide from excess reactant/precursor nucleotides. A noted benefit of solid-phase synthesis is the protection of reactive groups on the nascent oligonucleotide. Such protective groups are known to those of skill in the art, but may include, without limitation, 4,4'-dimethoxytrityl (DMT), benzoyl, isobutyryl, dimethylformamidyl, phenoxyacetyl, isopropyl phenoxyacetyl, and acetyl groups, and phosphate cyanoethyl protective groups (CNOEt). Solid-phase synthesis protocols, including protective groups and deprotecting methods, are well-known to those of skill in the art, and are typically automated procedures that can be conducted using commercially-available systems and reagents, such as those available from Asahi Kasei Bioprocess (Glenview, Ill.), Glen Research (Sterling Va.), BioAutomation Corp. (Plano, Tex.), and others. For additional background information on solid-phase synthesis of oligonucleotides, see Carriero et al. Soild-Phase Synthesis of Branched Oligonucleotides. In *Current Protocols in Nucleic Acid Chemistry*; John Wiley & Sons, Inc., Vol. 4 (2002).

Oligonucleotides formed according to these standard methods may be of any useful length. In certain embodiments, the oligonucleotide ranges in size from a 15-mer to a 70-mer, and all lengths in between, for example a 65-mer, 60-mer, 55-mer, 50-mer, 45-mer, 40-mer, 35-mer, 30-mer, 25-mer, or 20-mer. In one embodiment, the oligonucleotide is 20-25 residues in length, corresponding to a miRNA guide strand that is typically a substrate for RISC. In another embodiment, the oligonucleotide is a 22-mer.

During oligonucleotide synthesis on the solid-phase, nucleosides having a removable protecting group are included, or added to, the RNA chain. For formation of the lariat structure, this removable protection may be on the 2' position on the ribose sugar ring of a branched nucleotide (the nucleotide residue that includes 2', 3' and 5' linkages). For example, and without limitation, a photocleavable protecting group may be included at the 2' position. In such a system, exposure of the composition to a light source, for example ultraviolet (UV) light, cleaves the protecting group and leaves a reactive group, for example a 2'-hydroxyl group. Non-limiting examples of photoprotective groups include: 2-nitrobenzyl, 2-nitrophenyl ethyl, 2-nitrobenzyloxymethyl, 4,5-dimethoxy-2-nitrobenzyl (or 2-nitro-veratryl) and 4,5-dimethoxy-2-nitrobenzyloxymethyl (or 2-nitro-veratryl-oxymethyl (NVOM)).

Figure 2A:
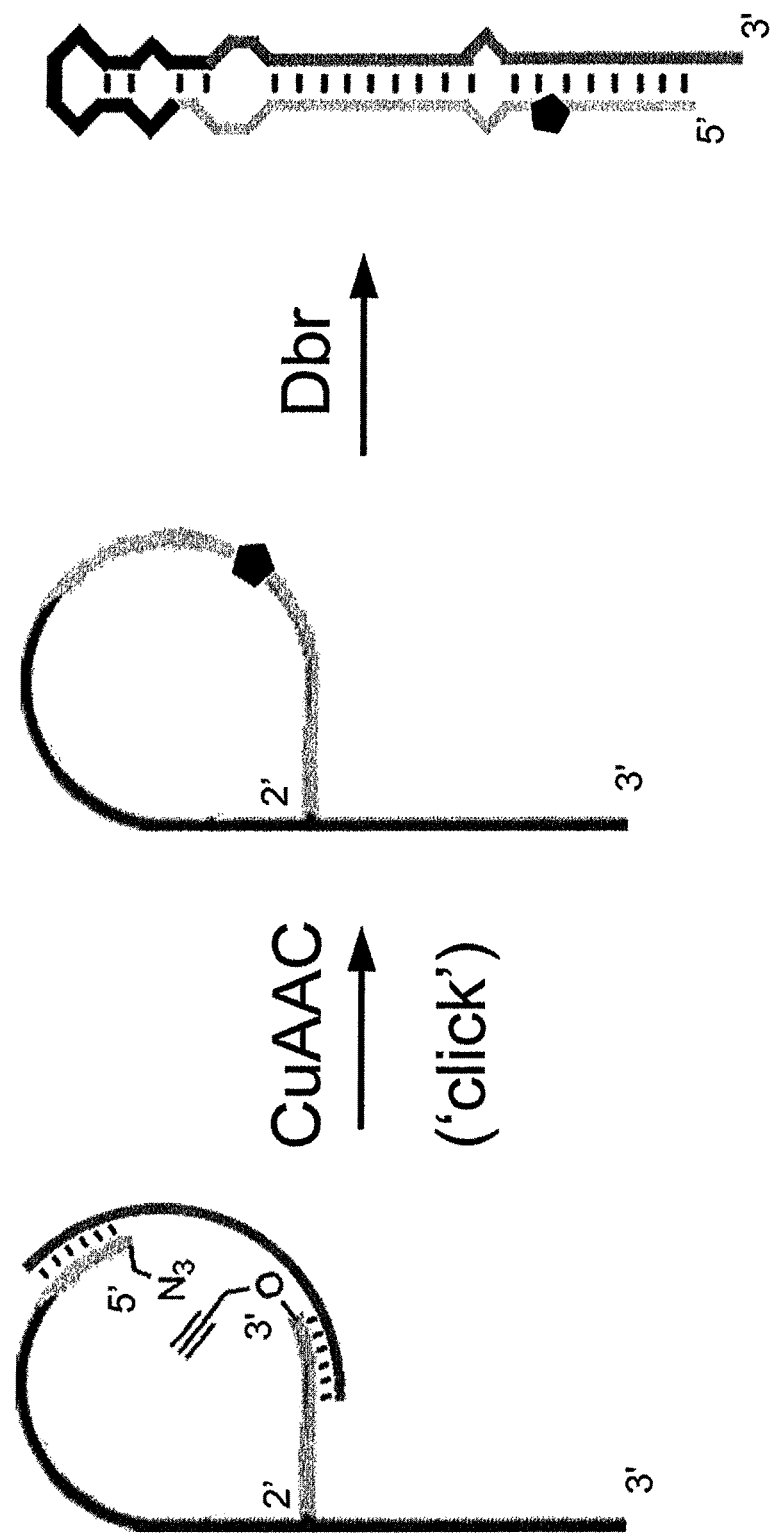
FIG. 2A-D shows solid-phase synthesis of lariat pre-miRNAs through bbNAs (backbone-branched nucleic acids) and click chemistry: A-B. Scheme for splinted click ligation and debranching by Dbr of (A) click-linked and (B) click-branched mirtronic lariats. C shows the sequence of the miR-1003 pre-miRNA used in for all the RNAi studies (SEQ ID NO: 1). The black pentagon denotes the triazole linkage in the click-linked mirtronic lariats. Circled A denotes branch-point adenosine and the bracket denotes the miRNA seed sequence; D. Native polyacrylamide gel (10%) used to resolve debranching reactions with Dbr (10 pmol) in 50 mM Tris.HCl (pH 7.5), $MnCl_2$ (10 nmol), DTT (2.5 nmol), and NaCl (250 nmol) for 10 mM at 30° C. Dbr is shown to debranch the lariat RNA1 (a(i)) which has a native branch-point, but not RNA2 (a(ii)), which carries a triazole-linked branchpoint. RNA3 is a transcribed pre-miRNA control which should run similar to the debranched mirtronic lariats.
Figure 2B:
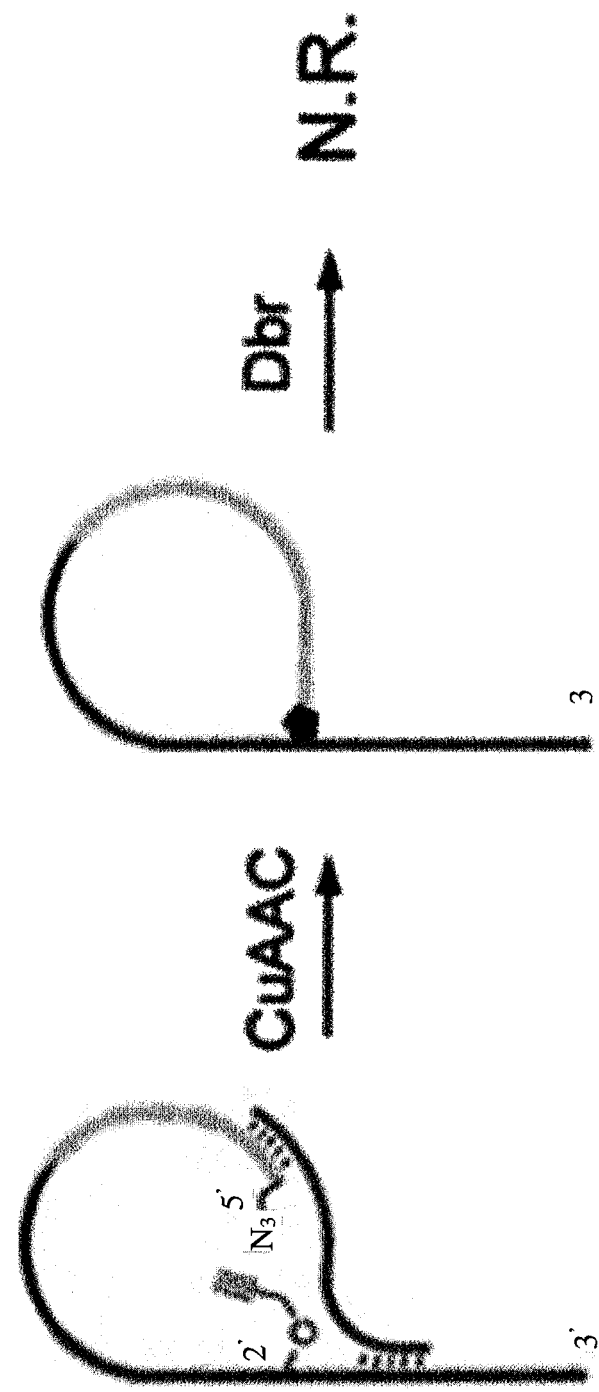
Figure 2C:
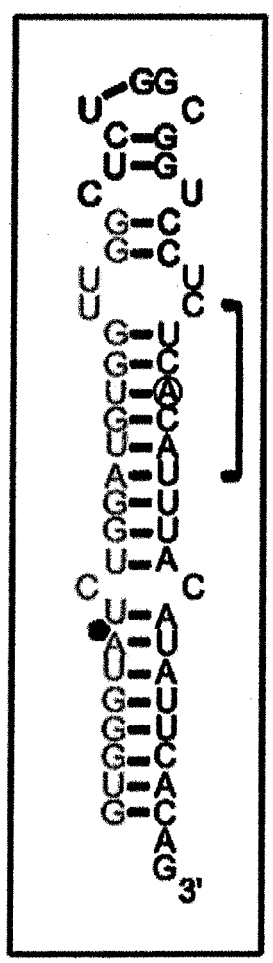

Additionally, the oligonucleotide may be branched during this solid-phase synthesis (see, e.g., FIG. 2A & FIG. 3B). The branch may be initiated at the de-protected 2' group of the ribose sugar, following deprotection by exposure to light, or any suitable deprotection protocol.

In some embodiments, an $N_3$ (azide) or alkyne group may be added to the 5' end of the oligonucleotide, with an alkyne (e.g., a terminal alkyne having the structure —CCH, for example and without limitation, a 3'-O-propargyl) group or azide group incorporated into a growing branch extending away (at the 2' position) from the linear first portion of the RNA oligonucleotide. In other non-limiting embodiments, the alkyne (e.g., 3'-O-propargyl) group is added by incorporation in the growing branch with a alkyne (e.g., 3'-O-propargyl) containing residue, which in one embodiment is an adenosine residue that is the branch (branch point). By providing the 5'-azide and the alkyne (e.g., 3'-O-propargyl) group in one embodiment or conversely the 5'-alkyne and 3'-azide, click chemistry reactions are possible that ligate the 5' end of the oligonucleotide to a branch extending from the oligonucleotide proper, to form a loop, and thus the lariat structure. (FIG. 2A & FIG. 3B).

As used herein, the term "click chemistry" refers to a high-yield reaction that allows for isolation/purification without the need for chromatography. Exemplary reactions that may be considered click chemistry include ring opening reactions (including of epoxides and aziridines), non-aldol type carbonyl reactions (such as formation of hydrazones and heterocycles), additions to carbon-carbon multiple bonds (such as oxidative formation of epoxides and Michael Additions), and cycloaddition reactions. International Patent Publication No. WO 2014/022720, incorporated herein by reference for its technical disclosure, discloses details of suitable click chemistries useful in the methods described herein (see, also, Paredes et al., "Optimization of Acetonitrile Co-solvent and Copper Stoichiometry for Psuedoligandless Click Chemistry with Nucleic Acids," (2012) *Bioorganic & Medicinal Chemistry Letters*, 22(16):5313-5316). Included in cycloaddition reactions of click chemistry are azide-alkyne cycloaddition, such as is possible through the 5'-azide and 3'-O-propargyl groups that may be added to the RNA oligonucleotide. These azide-alkyne cycloaddition ('click-chemistry') reactions may be catalyzed with Copper(I) compounds added directly or generated in situ from Copper (II) salts such as $CuSO_4$ and a reducing agent. For example, and without limitation, a click ligation reaction may involve a branched oligonucleotide having a 5' azide and a branch having a 3'-O-propargyl group in the presence of a copper catalyst, one or more DNA splints, sodium ascorbate or other reducing agent, copper (I) ligand or cetonitrile, and a buffer, for example, 1×PBS. (FIG. 2A).

The click reaction results in a triazole linkage (e.g.,

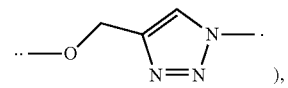

), thus a click-branched lariat will have the triazole linkage at the branch and this is not a substrate for Dbr. In contrast, the lariat that is formed by branching and then ligating the loop with the click reaction results in a lariat with a natural phosphodiester linkage at the branch and a click-(triazole) linkage in the loop. This click-linked lariat is a substrate for Dbr.

The nucleic acid lariat structures formed by the above-described oligonucleotide synthesis and click ligation reactions (click-linked lariats) are suitable substrates for Dbr, an enzyme that can be found in the cytoplasm of the cell. Debranching by Dbr allows the oligonucleotide to form a guide (active) strand for incorporation into RISC, similar to that seen in natively-occurring pri-miRNA that proceeds through the Drosha-Exportin pathway and becomes a substrate for Dicer. In contrast to the native miRNA mirtrons, however, the compositions described herein avoid Exportin and Dicer. Additionally, the above-described synthesis and ligation reactions are not the sole means for obtaining a lariat structure capable of avoiding the unwanted internal cellular mechanisms.

For example, in addition to click-chemistry reactions, nucleic acids having a lariat structure may be generated by linking the 5' end of the oligonucleotide to an unprotected 2' position on an internal nucleotide's ribose sugar through a standard, native phosphate linkage (through use of phosphoramidites), for example as shown in FIG. 3A. Such standard phosphoramidite chemistry and oligonucleotide synthesis is known to those of skill in the art. By generating a 5'-phosphoramidite and cleaving a protection group from a 2' position on the ribose sugar, the linkage occurs (FIG. 3A). In some embodiments, the 2'-protecting group is a photoprotector that is cleaved/deprotected through exposure to light, for example UV light, resulting in a reactive 2'-hydroxyl group. In other embodiments, the ligation may occur in the presence of an activator. In certain embodiments, the activator may be ethylthiotetrazole (ETT). Other activators, such as tetrazole, benzylthio-tetrazole or any other agents used to activate the phosphoramidite during the coupling reaction may be used. FIG. 3B shows a click-linked lariat as substantially described above, providing a triazole group at the ligation point.

Figure 4:
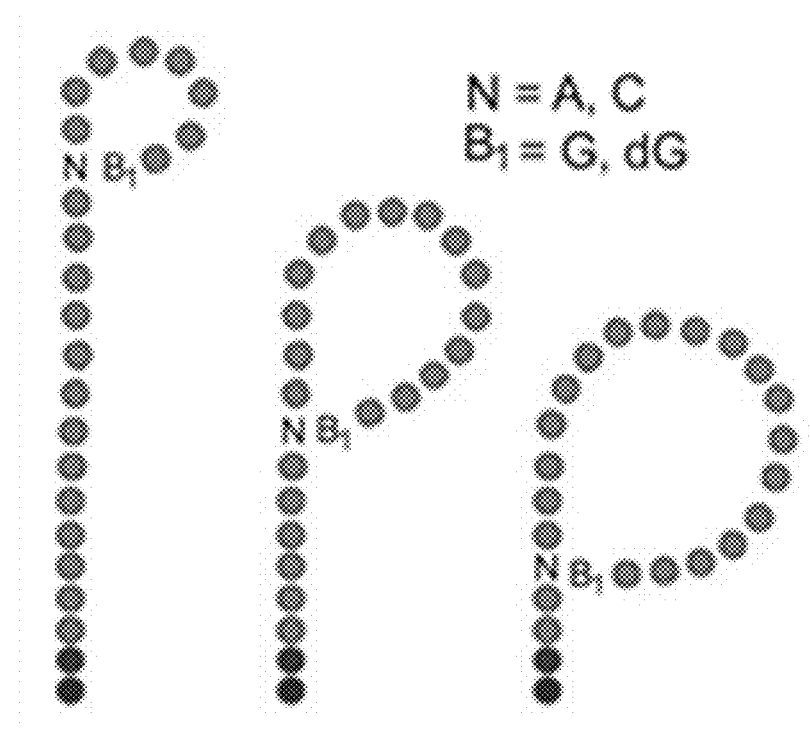
FIG. 4 shows examples of embodiments of the lariat structure of the present invention, with various loop sizes and internal modifications. In the illustrated embodiments, the last two residues at the 3'-terminus are 2'-deoxy residues to protect from exonucleases.

As described above, the oligonucleotide that forms the lariat may be of any useful size, and in one embodiment, is a 20-25-mer, for example a 22-mer—having a sequence that is at least partially complementary to, and preferably substantially (>90%) or completely complementary to an mRNA target to be knocked down by the RISC complex. The loop portion of the lariat structure may vary in size relative to the linear portion (FIG. 4). The loop may range from 3-20 nucleotides in length. In one embodiment, the loop is from 3-15 nucleotides in length, for example 5, 10, or nucleotides in length. In the illustrated embodiments, for knocking down luciferase, the anti-luciferase sequences is 5'-UUG AUU AAC GCC CAG CGU U tt-3' (SEQ ID NO: 3) with bold A and C indicating potential branch-points that will lead to loop sizes of 3, 6, 11 or 15 (the lower-case 't' denotes the deoxyribonucleotide residues incorporated as protective groups for the 3' end of the structure). In another embodiment based on FIG. 4, an additional modification is a phosphorothioate modification in the 2'-5'-linkage between N (the branching nucleotide) and B1.

Figure 5:
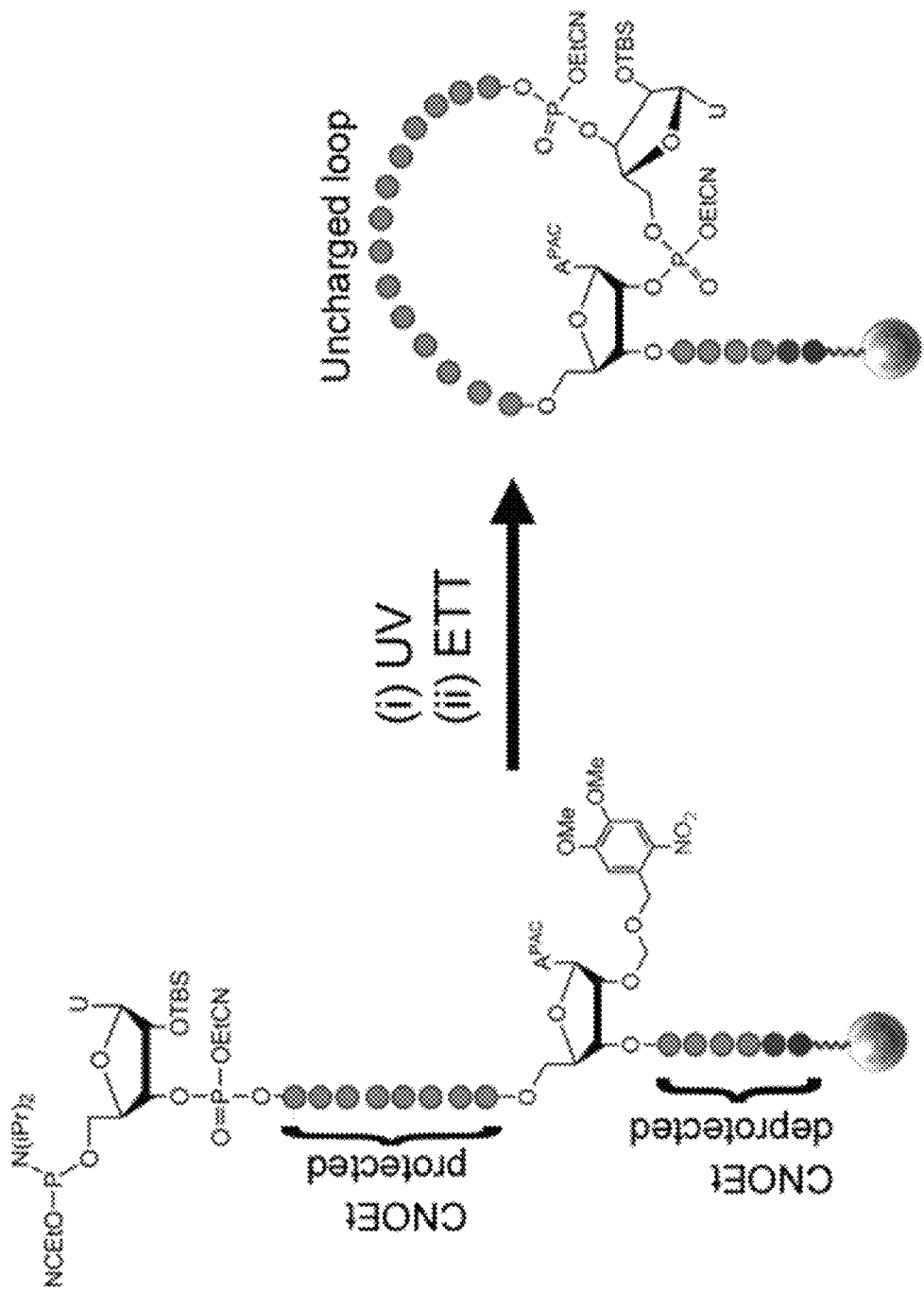
FIG. 5 shows an embodiment of a cyclization reaction to provide a nucleic acid lariat according to one embodiment of the present invention.

Two additional methods of cyclization (forming the lariat) based on the use of a standard, phosphate linkage are also possible. In the first, the CNOEt protective groups are removed from the oligonucleotide only on residues 3' to the branching residue This selective removal, by use of any suitable removing/deprotection agent, such as triethylamine and/or acetonitrile, results in a linear portion having a stable phosphodiester linkage (preventing attack by a deprotected 2'-hydroxyl group of the branch point residue) and a loop portion (residues 5' to the branch point residue) that includes uncharged phosphotriester linkages with protective CNOEt groups (FIG. 5).

Figure 6:
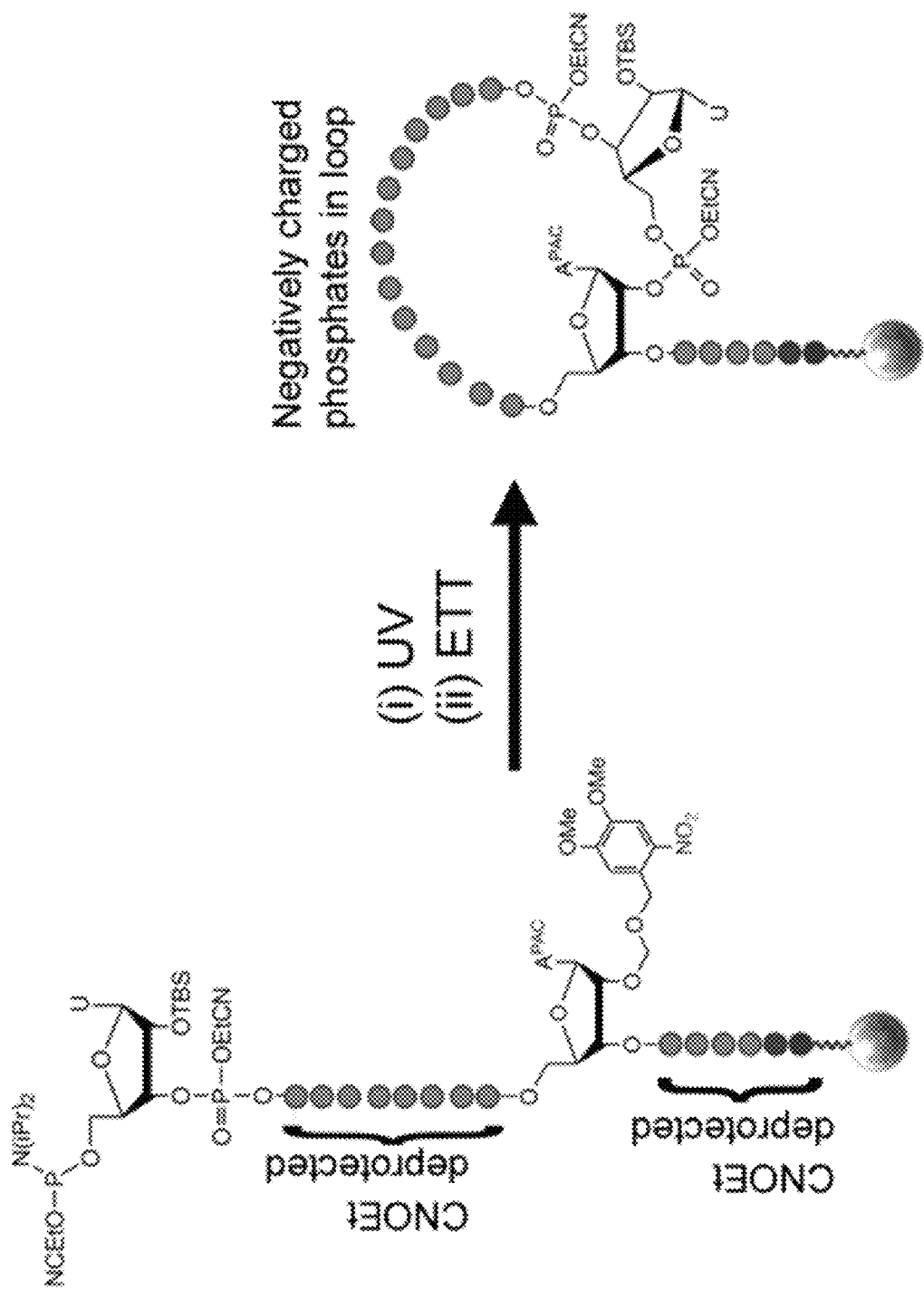
FIG. 6 shows an embodiment of a cyclization reaction to provide a nucleic acid lariat according to one embodiment of the present invention.

In yet another embodiment, the entire oligonucleotide is subjected to CNOEt deprotection prior to activation of the 5' phosphoramidite, resulting in a oligonucleotide will have a phosphodiester (charged) backbone, and thus a loop portion (5' to the branch point residue) that is also charged (FIG. 6).

No matter the synthesis method utilized to provide the nucleic acid lariat structure, further modifications to the oligonucleotide may be undertaken to prolong the efficacy of the composition for modifying gene expression. For example, and without limitation, the 3' end of the oligonucleotide may be protected, that is, modified to inhibit degradation by nucleases, or may also include a 3'-terminal fluorescent dye. Protection of the 5' end is achieved by the lariat structure, but the 3' end may be vulnerable to nucleases which could shorten the effective life of the compositions of the present invention. In one embodiment, the 3' end of the oligonucleotide is protected by addition of a non-ribonucleotide monomer or group, such as, without limitation, deoxynucleotides (e.g., 2' deoxy) and/or aryl units. In one embodiment, at least one deoxynucleotide is added to the 3' end of the oligonucleotide during or after synthesis of the lariat structure, for example by first adding one or more deoxyribonucleotide residues during solid-phase synthesis prior to addition or ribonucleotide residues. In one embodiment, the deoxynucleotide is L-deoxycytosine. In further embodiments, a plurality of L-deoxyribonucleotide residues are added to the 3' end of the oligonucleotide.

Uses for Nucleic Acid Lariats

The synthetic nucleic acid lariat structures described herein may be utilized in vitro, ex vivo, or in vivo in any cell/tissue or organism that would benefit from the modification of expression of a gene, for example silencing, or knocking down, of a particular gene for any therapeutic or research purpose. For example, and without limitation, the synthetic nucleic acid lariat may be used in animals, including mammals such as human, in plants, and in yeast. Oligonucleotide sequences to match (anti-sense) the mRNA of the gene of interest can be designed based on the sequence of the gene/mRNA of interest. Sequencing of gene(s) of interest, and ascertaining their expression levels, e.g., by Southern Blot or quantitative PCR techniques, such as quantitative reverse transcription PCR (QRT-PCR, e.g. TAQMAN®) are standard in the art and do not require any undue effort or experimentation.

When used in mammals, for example humans, the synthetic nucleic acid lariat structures described herein may be used for prevention and/or treatment of a wide variety of diseases, through gene knockdown, silencing or interference, as is known to those of skill in the art. As used herein, "treatment" means therapeutic uses and "prevention" means prophylactic uses. For example, and without limitation, the synthetic nucleic acid lariat structures of described herein may be utilized in the prevention and/or treatment of various types of cancers, through silencing genes responsible for the production of proteins or non-coding RNA that increase tumorogenicity, invasiveness of cancer cells, or the like, including melanoma (superficial spreading, lentigo, acral lentiginous, and/or nodular), basal cell carcinoma, squamous cell carcinoma, adenocarcinoma (p53), adenosquamous carcinoma (SKA1), anaplastic carcinoma (OEATC-1), large cell carcinoma, small cell carcinoma, prostate cancer (K-ras), breast cancer (K-ras), ovarian cancer (WAVE1), cervical cancer (AKAP4), pancreatic cancer (galectin-3), gallbladder cancer (SNCG), bladder cancer (survivin) testicular cancer (p53), mesothelioma (mesothelin), non-small cell lung cancer, small-cell lung cancer, thyroid cancer (OEATC-1), glioblastoma (thymosin beta 4). miRNA precursors described herein would typically include 18-25 contiguous bases of miRNA guide sequences of miRNAs, such as any 18-25 contiguous bases of the miR644a, Let-7 and Mir17 sequences that follow. Non-limiting examples, sequences of miRNAs with therapeutic potential, which are related to targets such as miR644a—implicated with androgen receptor and prostate cancer and other oncogene miRNAs are:

```
miR644a:
                                             (SEQ ID NO: 4)
5'-AGU GUG GCU UUC UUA GAG,

Let-7:
                                             (SEQ ID NO: 5)
AUGAGGUAGUAGGUUGUAUAGUUUUAGGGUCACACCCCUAUACA

AUCUACUGUCUUUC,
and

Mir17
                                             (SEQ ID NO: 6)
CAAAGUGCUUACAGUGCAGGUAG.
```

Silencing by the synthetic nucleic acid lariat structures described herein can also be utilized to combat drug resistance in cancer, for example, and without limitation, by targeting specific proteins, such as MDR1 or ERa in drug-resistant breast cancer. In other embodiments, silencing through use of the present synthetic nucleic acid lariat structures can be coupled with introduction of "replacement" genes, to knockdown or silence mutant alleles while allow for production of proteins through transcription and translation of wild-type alleles (through a silent mutation (synonymous substitution) in the antisense strand).

While the above examples involves silencing or knocking down production of a protein through interaction with a gene/gene transcript, it will be understood by those of skill in the art that the synthetic nucleic acid lariat structures of the present invention can be used to modify expression of genes in a manner that will result in upregulation, or overexpression, of non-targeted protein(s).

In commercial uses, gene silencing can be used to control expression of certain genes, for example in yeast or mammalian cultures. For example, a gene may repress expression of a desired product, or may otherwise interfere with obtaining a pure gene product in sufficient quantities. Virtually any gene or set of genes can be targeted in this manner so as to produce or shut down undesirable gene expression. In one example, a metabolic product may be enriched by silencing expression of enzymes that degrade that product.

In addition to prevention and/or treatment of cancer, the synthetic nucleic acid lariat structures described herein are also useful in the prevention and/or treatment of additional diseases/conditions. These diseases/conditions include, but are not limited to, Parkinson's Disease (α-synuclein), Amyotrophic Lateral Sclerosis (SOD1), Huntingdon's Disease (huntingtin), autoimmune disorders such as arthritis (IL-12), rheumatoid arthritis (TNF-α), and multiple sclerosis (IL-12), asthma (Rip2), allergies (STATE), pain (including idiopathic pain such as fibromyalgia), spinocerebellar ataxia (ATXN) cardiovascular diseases/conditions (including dyslipidemia and/or hypercholesterolemia (ApoB)), diabetes (IL-12), wound healing (PHD2), and/or AIDS (HIV-1). As with treatment of cancer, the synthetic nucleic acid lariat structures described herein may also be used to silence expression of specific proteins that impart drug resistance, for example resistance to antibiotics (bcl-2).

Those of skill in the art understand that identification of genes that are upregulated in a condition or disease is routine, and sequences that would silence those genes may be designed based on the identification of those genes with minimal effort.

Methods of Delivery of Nucleic Acid Lariats

The synthetic nucleic acid lariat structures described herein may be delivered to a cell or an organism, such as a mammal, plant, yeast, or other organism, in any suitable manner known to those of skill in the art for delivery of a product to the cytoplasm of a cell, where the lariat structure can function to silence a gene at the translational stage. These structures can be delivered directly to a subject by any route known to those of skill in the art, including orally or parenterally. Parenteral routes of administration may include any type of injection, for example intramuscular, subcutaneous, or intravenous. Administration may also be transdermally or by inhalation, insufflation, and/or absorption through mucosa. The product to be delivered, in one embodiment, includes the synthetic nucleic acid lariat structure in a delivery vehicle, for example and without limitation, a liposome or nanosome.

As used herein, the term liposome refers to any vesicle having a lipid bilayer. The typical liposome contains phospholipids, for example phosphatidylcholine-rich phospholipids, but may also include other constituents for directing delivery to one particular cell type or another, for example cationic phospholipids and/or anionic phospholipids. Liposomes may be prepared as known to those of skill in the art (see, *Remington: The Science and Practice of Pharmacy,* 21st edition, ed. Paul Beringer et al., Lippincott, Williams & Wilkins, Baltimore, Md. Easton, Pa. (2005), pp. 766-767) Additionally, a liposome may further include cholesterol constituents in the lipid bilayer. As used herein the term nanosome refers to a liposome having a diameter in the nanometer size range, for example from about 0.01 to about 1,000 nm. The nanosome includes a lipid bilayer and may optionally include other constituents, such as cholesterol.

In addition to inclusion in a liposomal or nanosomal structure, the synthetic nucleic acid lariat structures described herein may also be encapsulated in particulate carriers. These carriers may be formed from any biocompatible, biosafe, biodegradable, tolerable substance, for example and without limitation biosafe polymers. Such polymers include, without limitation, poly(lactic acid) or poly(lactide) (PLA), and poly(lactide-co-glycolic acid) or poly(lactide-co-glycolides (PLGA), methyl methacrylate, poly(methyl methacrylate), ethyl acrylate, polyamines such as polylysine, polyarginine, polyornithine, spermine, and spermidine, chitosan/triphosphate particles, and the like. Design of particulate carriers is known to those of skill in the art, and may include analogues, derivatives, and conjugates of the previously-mentioned materials, and additionally may include coatings, for example hyaluronic acid coatings.

The above-described delivery vehicles can be formulated for delivery in a manner known to those of skill in the art. For example, and without limitation, therapeutic/pharmaceutical compositions are prepared in accordance with acceptable pharmaceutical procedures, such as described in *Remington: The Science and Practice of Pharmacy,* 21st edition, Chapters 37, 39, 41, 42 and 45 for examples of powder, liquid, parenteral, intravenous and oral solid formulations and methods of making such formulations). Any of the compounds described herein may be compounded or otherwise manufactured into a suitable composition for use, such as a pharmaceutical dosage form or drug product in which the compound is an active ingredient.

According to one example, the drug product described herein is an oral tablet, capsule, caplet, liquid-filled or gel-filled capsule, etc. Compositions may comprise a pharmaceutically acceptable carrier, or excipient. An excipient is an inactive substance used as a carrier for the active ingredients of a medication. Although "inactive," excipients may facilitate and aid in increasing the delivery, stability or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

The formulation may also be delivered by any suitable inhalation or insufflation delivery system. For example and without limitation, a nebulizer or atomizer, a dry powder inhaler, a nasal inhaler and a metered dose aerosol inhaler, as are broadly known in the pharmaceutical arts, may be used (see, *Remington: The Science and Practice of Pharmacy,* 21st edition, pp. 1000-1017, Chapters 37 and 39).

In another embodiment any compound as described herein is provided and delivered in a transdermal device. Suitable structures and compositions for such a device are well-known in the pharmaceutical arts, generally including an occluding backing comprising an adhesive on one side to face a patient, and a drug reservoir on the same side of the occluding backing as the adhesive. The reservoir may be a non-woven fabric or gauze, or a hydrogel in which an active agent, such as any composition described herein may be absorbed or admixed. Often a permeation enhancing compound is includes in the reservoir to facilitate transfer of the active agent into/through the skin (see, e.g., *Remington: The Science and Practice of Pharmacy,* 21st edition, Chapter 65).

Figure 7:
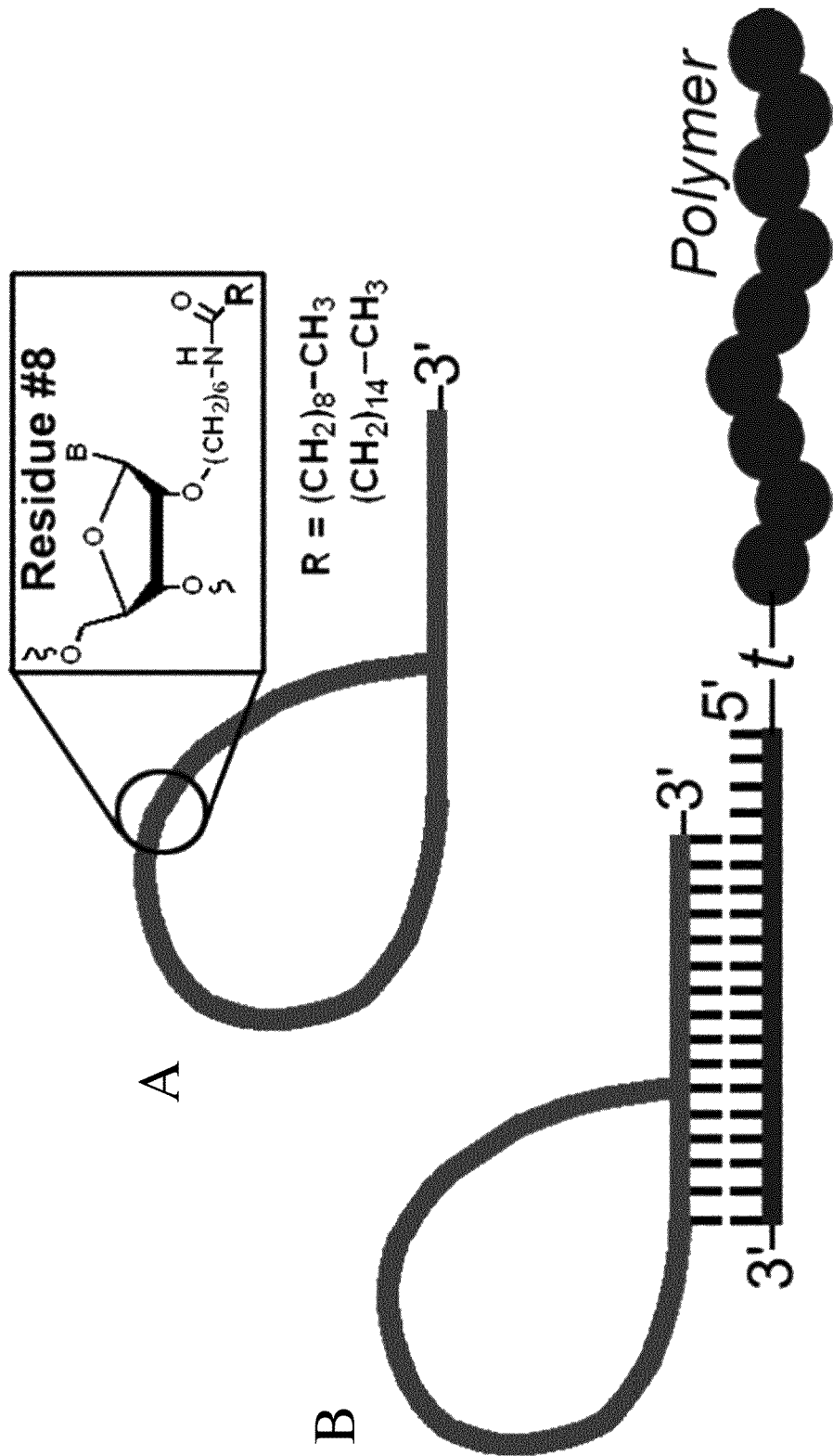
FIG. 7 shows embodiments of modifications of one embodiment of a nucleic acid lariat according to the present invention: A. O-lipidoylation of a residue; B. a carrier strand polymer escort.

In addition to the liposomal and other delivery methods described above, the synthetic nucleic acid lariat structures described herein may linked to a delivery vehicle and thus be delivered to the cell of any organism by modification of the oligonucleotide itself. In one embodiment, the oligonucleotide may be subjected to lipid modification (FIG. 7A). In certain embodiments, this lipid modification may involve modification at the 2'-oxygen of any nucleotide of the oligonucleotide. In certain embodiments, the 2'-O-lipid modification occurs at a nucleotide in the loop portion of the lariat structure. In further embodiments, the 2'-O-lipid modification occurs at the eighth residue of the loop.

Figure 8:
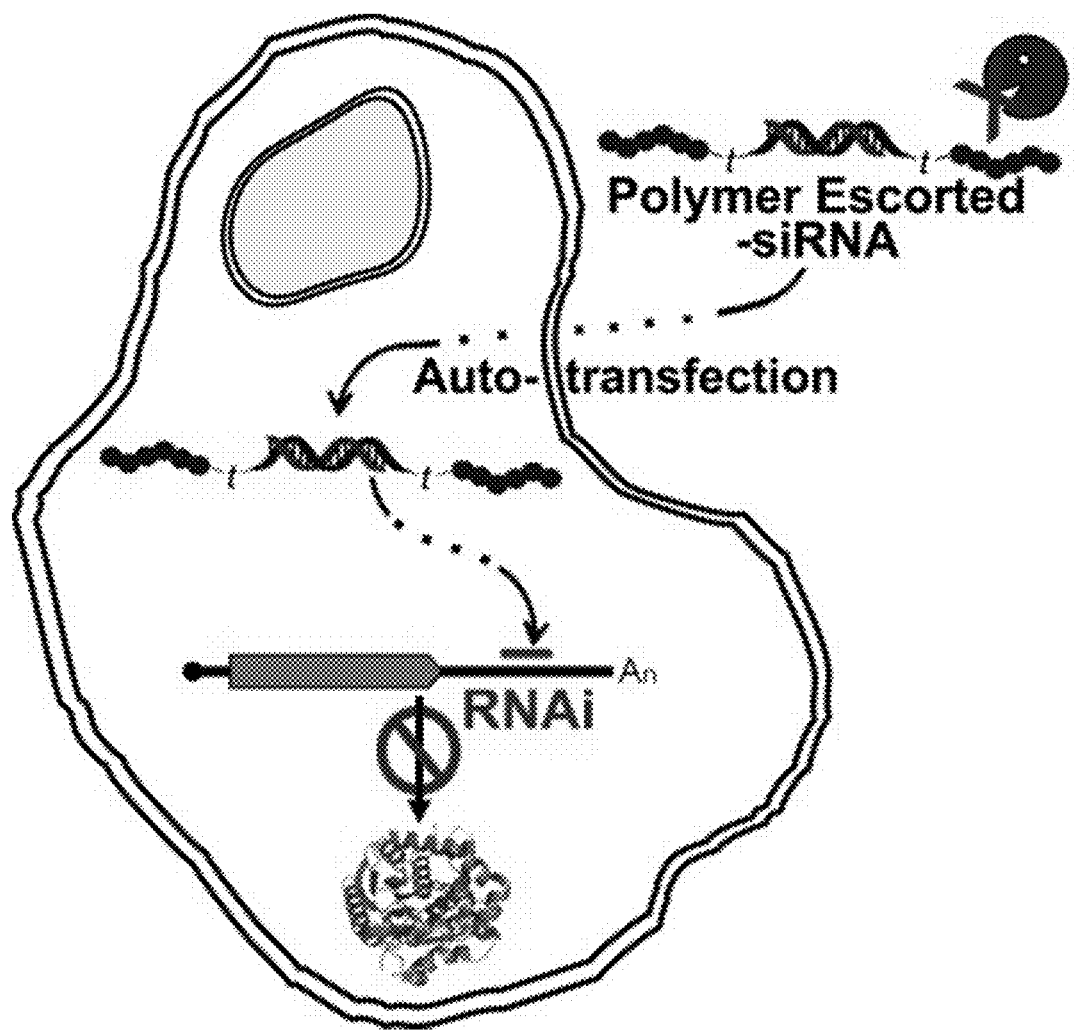
FIG. 8 shows an illustration of an auto-transfection pathway of one embodiment of the modification of a nucleic acid lariat shown in FIG. 7b.

Yet another possible modification of the oligonucleotide itself is to add a modified carrier strand to the single-stranded nucleic acid (FIG. 7B). In certain embodiments, the single-stranded RNA described herein may be introduced into a cell with a second, carrier strand. This carrier strand may be modified in any number of ways known to those of skill in the art. In one embodiment, the carrier strand is conjugated to a polymer escort (FIG. 7B & FIG. 8). The polymer(s) useful for this process include, but are not limited to pOEOMA475-co-pDMAEMA (poly(oligo(ethylene oxide) monomethyl ether methacrylate and dimethylaminoethyl methacrylate), NIPAAM (N-isopropylacrylamide), PAMPTMA (polyacrylamidopropyl trimethylammonium chloride), lipids and lipid-like lipidoids. Any polymer that aids in internalizing the nucleic acid lariat structure will be useful in the methods and compositions of the present invention. Polymers that include ionizable dimethylamine groups may be particularly well suited to this purpose (see Averick et al. Autotransfecting Short Interfering RNA Through Facile Covalent Polymer Escorts. *J. Am. Chem. Soc.* 135: 12508-12511 (2013)).

EXAMPLES

Example 1

To overcome the challenging delivery of RNA constructs in current RNA interference therapy, a single stranded (ss) siRNA was developed and synthesized in the solid phase to form an RNA lariat.

In one example, the solid-phase synthesis of lariat RNAs, demonstrated in FIG. 3, is carried out by an internal 2'-O-photoprotecting group. Following the synthesis of the linear RNA, 5'-phosphoramidite synthesis on the solid-phase followed by selective UV deprotection and further amidite activation, yield the lariat RNA. Additionally, the solid-phase synthesis of click lariat RNAs (FIGS. 3A & 3B) is carried out by synthesizing a branch with a 5'-azide cap and a 3'-O-propargyl group on the branch incorporated using additional protocols developed in our lab. A CuAAC reaction in the solid-phase yields the click lariat RNA. Removal from the solid support, deprotection and purification of these lariats is carried out with standard protocols.

Figure 9:
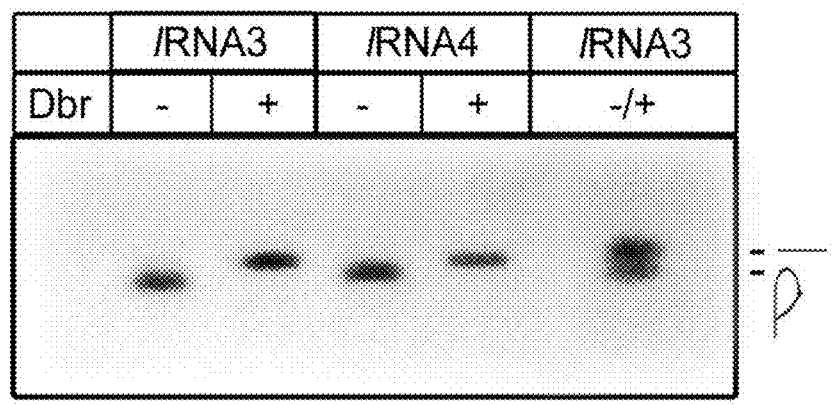
FIG. 9 shows a polyacrylamide (20%-8M Urea) gel used to resolve debranching reactions with lariat RNA3 and click lariat RNA4. −/+ lane indicates a co-loading of two reaction mixtures to confirm that the two bands observed in the (−) and (+) lanes are distinct RNAs.

In another example, experiments using Dbr enzyme in aqueous buffer confirmed that these example RNAs (labeled/RNA3 and /RNA4) are efficiently debranched by Dbr enzyme, as shown in FIG. 9. The last experiment shown, represented by the −/+ lane, indicates a co-loading of two reaction mixtures to confirm that the two bands observed in the (−) and (+) lanes are distinct RNAs.

Figure 10:
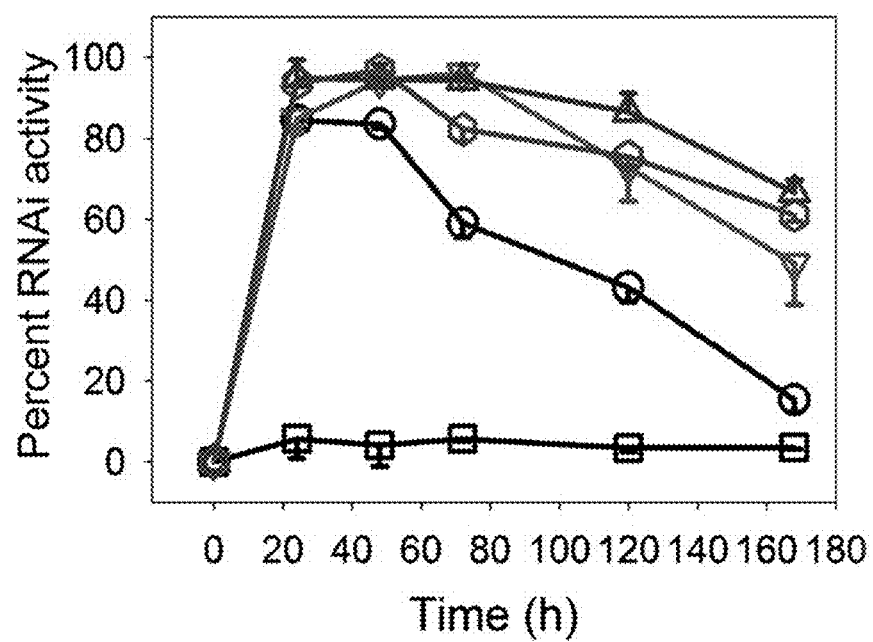
FIG. 10 shows a plot of RNAi activity of the lariat (triangles and trace) and click lariat (hexagon and trace) synthesized examples compared to the ss siRNA (circles and trace), the ss siRNA (squares and trace), and the duplex siRNA (upside down triangles and trace) in dual-luciferase reporter assays in S2 cells.
Figure 11A:
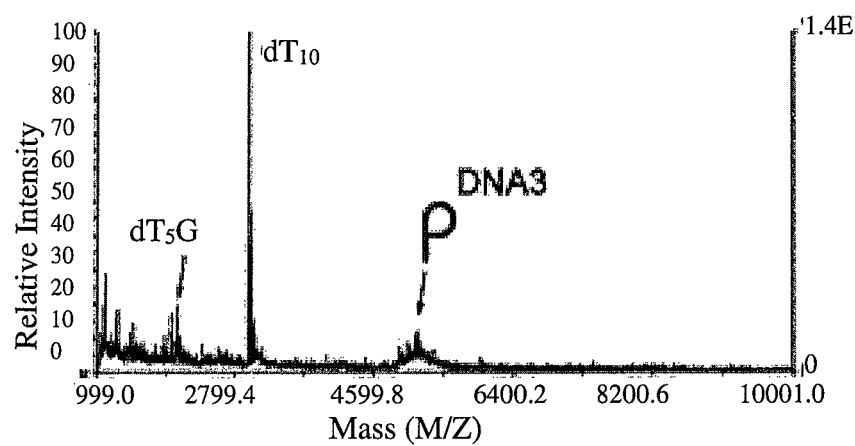
FIG. 11A-C shows solid-phase synthesis of lariat DNAs is efficient: A.-C. MALDI spectra of a. DNA3, b. DNA4, and c. DNA5 show that although lariat DNAs are being synthesized without many side-products, products due to cleavage at the branch points are observed.
Figure 11B:
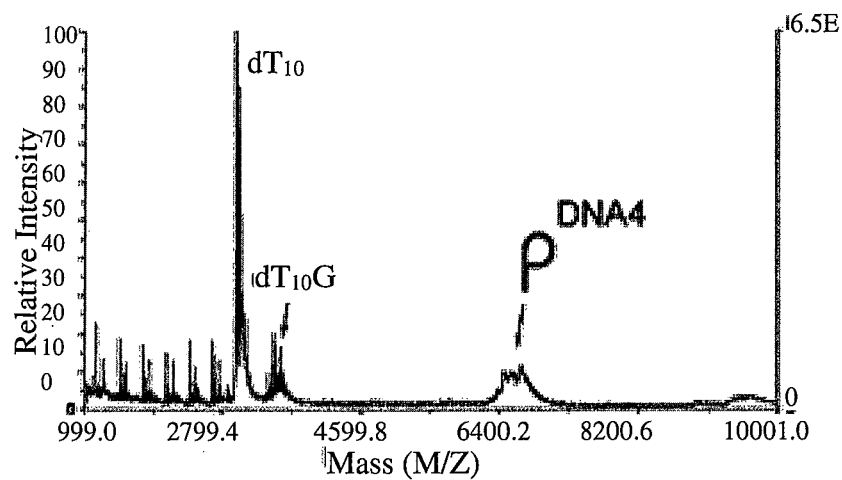
Figure 11C:
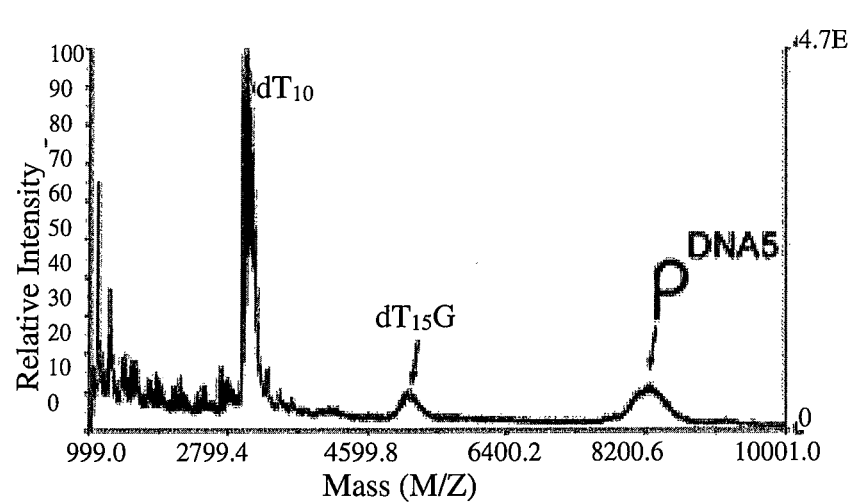
Figure 12A:
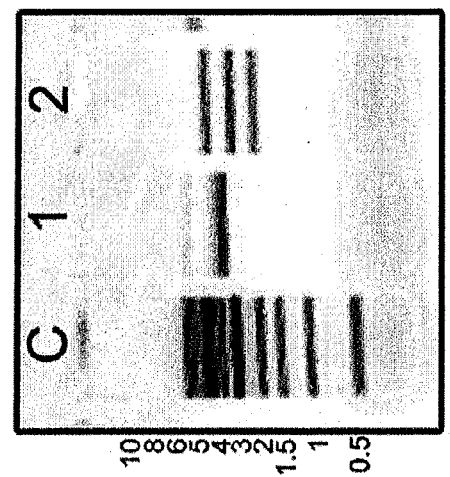
FIG. 12A-B shows plasmid reporters have luciferase genes of expected length following re-transformation. A., B. CJ22 (Rluc) or pGL3 (Fluc) reporter plasmid restriction schemes with BamH1, Xho1 and Kpn1 as mentioned. Insets show 1% Agarose gels used to resolve restriction reaction mixtures. Lane C denotes 10 kb ladder control, Lane 1 denotes unrestricted plasmids and Lane 2 denotes double restriction reaction mixture. Arrows denote full-length luciferase gene fragment as expected.
Figure 12A:
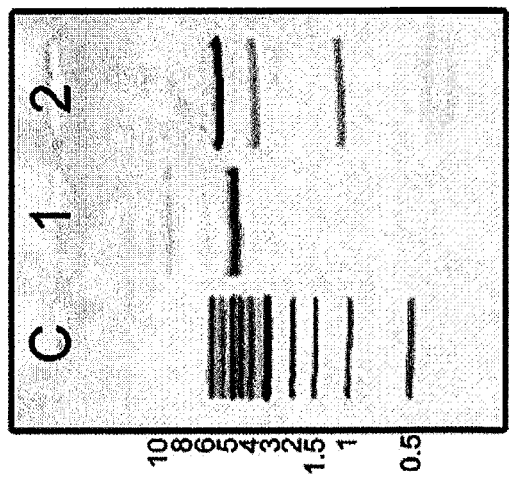
Figure 12A:
Figure 12A:
Figure 12A:
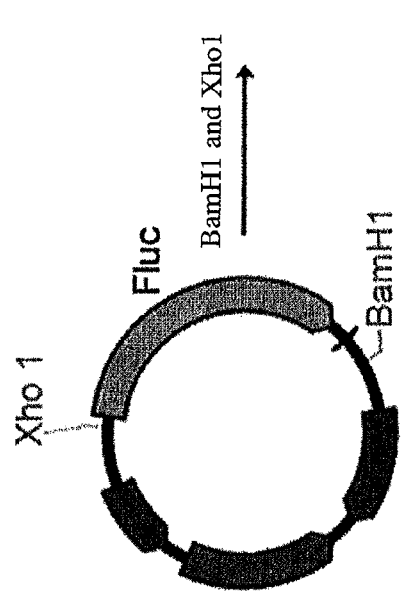
Figure 12B:
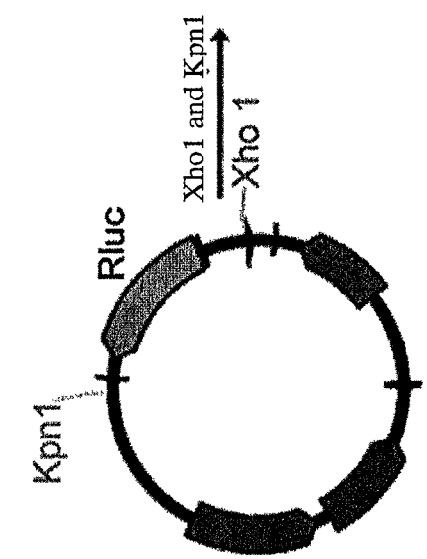

In another example, the lariat RNAs were transfected into S2 cells from *drosophila* to test their ability to induce RNAi against a luciferase reporter (FIG. 10). It was demonstrated that these example lariat RNAs (triangle and hexagon) are as potent as their linear counterparts (circle). Additionally it was found that the effect of these lariat RNAs persists longer than their linear counterparts (upside down triangle and circle) and is similar than the duplex siRNA (upside down triangle). Together with the ease of synthesis, and the potential for additional modifications in the RNA that can confer additional stability and other properties for enhanced delivery, this approach to RNAi induction by synthetic lariat RNAs is more advantageous than other RNAi induction methods.

Example 2

Solid-Phase Synthesis of Lariat Pre-miRNAs Through bbNAs and Click Chemistry

As mirtrons are generally excised from pri-mRNA as hairpins containing both the guide and the passenger sequence, we sought to synthesize a ~60-mer RNA lariat in the solid-phase. Synthesis of such a large RNA construct is challenging given the traditional length constraints of this synthesis approach. Undeterred by this challenge, we synthesized backbone-branched RNA1,2 precursors for lariat synthesis. In these precursors, a 5'-azide was furnished on the solid phase (Miller et al. Versatile 5'-Functionalization of Oligonucleotides on Solid Support: Amines, Azides, Thiols, and Thioethers via Phosphorus Chemistry. *J. Org. Chem.* 69: 2404-2410 (2004)) and a 3'-O-propargyl was incorporated in the final branch synthesis steps using a 2'-3'-dideoxy-3'-O-propargyl-5'-CED adenosine (n-Bz) phosphoramidite. Following removal from the solid-support and deprotection, splinted click ligation reactions (FIG. 2A) yield the (i) click-linked and (ii) click-branched mirtronic lariats. Although the synthesis of such large constructs is possible in the solid-phase, the recovered yields from the syntheses is on average 0.14±0.03% (N=2). With such inefficient yields, the synthesis of these mirtronic lariats for RNAi studies is not possible. However, with the little material we recovered, we carried out debranching reactions with trace amounts of radiolabeled lariat RNAs to test Dbr activity against the synthesized lariats. We found that while the lariat RNA1 gets debranched by Dbr to an RNA that run similar to a corresponding transcribed pre-miRNA, RNA3, the click-branched RNA2 is not cleaved by Dbr. This suggests that synthetic lariats are substrates to Dbr when they do not include a triazole linkage at the branch point.

Solid-Phase Synthesis of Lariat siRNAs Using Click Chemistry and Photo-Protecting Groups Experimental Procedures Chemicals and General Experimental Commercially available compounds were used without further purification. The L-deoxycitidine phosphoramidite and solid supports and were purchased from ChemGenes. Phosphoramidic chloride was purchased from ChemGenes. N,N-diisopropylethylamine, 1-methylimidazole, and dichloromethane (DCM) were purchased from Fisher. CJ22 *renilla* luciferase reporter plasmid was purchased from AddGene. pGL3 firefly luciferase reporter plasmid, FuGENE HD® and Dual Glow Luciferase® system were purchased from Promega. Other solvents and reagents not otherwise specified were purchased from Fisher.

Nucleic Acid Synthesis and Preparation

Synthesis of linear oligonucleotides was conducted using standard protocols for PAC protected amidites as recommended by the manufacturer. When incorporating the photocleavable 2'-protecting group and branching of oligonucleotides, the appropriate were used following standard protocols. The RNA sequences used in this study are summarized in Table 1, below. When necessary, 3'-end radiolabeling was carried out using Poly (A) pol and $[\alpha\text{-}^{32}P]$ cordycepin using standard protocols recommended by the manufacturer.

TABLE 1

RNA sequences used in this study

| Name | Sequence | Mass Calc | Mass Found |
|---|---|---|---|
| RNA1 | 5'-N$_3$-UCUGGAUGUGGUUGGCUCUGGCGGUCCUCUCA(2'-GUGGGUA-3'-O-propargyl)CAUUUACAUAUUCACAG -3' | 17894.23 | 17901.3 |
| RNA2 | 5'-N$_3$-GUGGGUAUCUGGAUGUGGUUGGCUCUGGCGGU CCUCUCA(2'-O-propargyl)AUUUACAUAUUCACAG -3' | 17878.25 | 17878.0 |
| DNA1 (SEQ ID NO: 7) | 5'- aaccacatccagatacccac-3' | IDT | |
| DNA2 (SEQ ID NO: 8) | 5'-tgtaaatgcacccatagacc-3' | IDT | |
| RNA3 (SEQ ID NO: 9) | 5'PO$_4$GUGGGUAUCUGGAUGUGGUUGGCUCUGGC GG UCC UCUCACAU UUACAUAUUCACAG -3' | Transcription with GMP | |
| RNA4 (SEQ ID NO: 10) | 5'- CUCACAUUUACAUAUUCACAG-3' | 6558.9 | 6560.7 |
| RNA5 (SEQ ID NO: 11) | 5'- GUGGGUA UCUGGAUGUGGUU-3' | 6454.8 | 6457.6 |
| RNA6 | . . . CAUUUACAUA(2'-5'UCUCA-$_t$)UUCAC~~CC~~-3' | 6882.9 | 6882.5 |
| DNA3 | . . . tttG(2'-5'-tt$_p$ . . .)tttttttttt | 4910.1 | 4914.6 |
| DNA4 | . . . tttttttG(2'-5'-tt$_p$ . . .)tttttttttt | 6431.1 | 6433.5 |
| DNA5 | . . . tttttttttttttG(2'-5'-tt$_p$ . . .)tttttttttt | 7952.1 | 7960.9 |
| RNA7 | . . . UCUCACAUUUACAUA(2'-5'-$_p$ . . .)UUCAC~~CC~~-3' | 6880.9 | 6883.2 |

$_t$-denotes triazole linkage and $_p$-denotes native phosphate linkage. Strikethrough denotes L-deoxy residues Synthesis of Click-Linked and Click-Branched Mirtronic Lariats Following solid-phase synthesis of RNA1,2 precursors, the 5'-N$_3$ was furnished on the solid-phase by adapting literature reports (see, Miller et al. Versatile 5'-Functionalization of Oligonucleotides on Solid Support: Amines, Azides, Thiols, and Thioethers via Phosphorus Chemistry. *J. Org. Chem.* 69: 2404-2410 (2004)). Following azide synthesis, the installed 2'-photoprotecting group was removed using UV light for branch synthesis. Incorporation of a 3'-O-propargyl group within the RNA branch was achieved by coupling of the growing oligonucleotide branch with a 2'-3'-dideoxy-3'-O-propargyl-5'-CED adenosine (n-Bz) phosphoramidite in the solid-phase following standard protocols for branching amidites. Following synthesis and standard deprotection, purification and desalting of clickable branched RNA1,2 we obtained 1.66 nmol and 1.16 nmol out of 1 µmol synthesis columns corresponding to isolated yields of 0.16% and 0.11% respectively. The RNA branches (100 pmol) were click ligated with the use of a DNA1,2 splints (200 pmol) respectively using CuSO$_4$ (1 nmol), sodium ascorbate (5 nmol) in 1×PBS with 1% ACN at 4° C. with shaking for 3 h. The reaction mixture was desalted and the RNAs were 3'-end radiolabeled with [α-$^{32}$P] cordycepin using standard protocols and purified on a polyacrylamide gel (10%-8M Urea).

Debranching of Click-Linked and Click-Branched Mirtronic Lariats

Figure 2D:
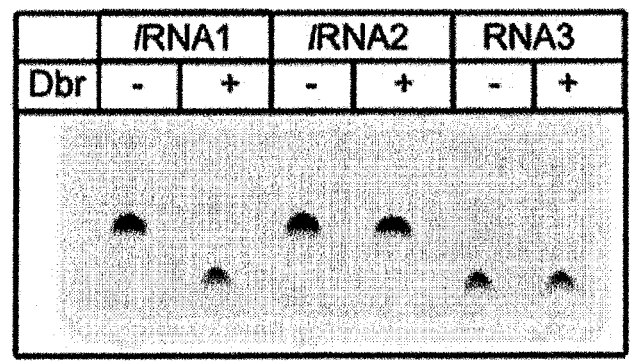

Trace amounts of click ligated RNA1, RNA2 or RNA3 (linear control transcript) were incubated with Dbr (10 pmol) in a solution of 50 mM Tris.HCl (pH 7.5), MnCl$_2$ (10 nmol), DTT (2.5 nmol), and NaCl (250 nmol) for 10 min at 30° C. The reaction mixtures were loaded on a native polyacrylamide gel (10%-8M Urea) to resolve the debranching reaction mixtures FIG. 2D.

Solid-Phase Synthesis of Branched Nucleic Acids for Click Lariat ss siRNA Synthesis Following solid-phase synthesis of RNA6 precursor, the 5'-azide synthesis, branch synthesis and 3'-O-propargyl incorporation were carried out as mentioned before. Following branch synthesis, click ligation on the solid-phase was achieved by addition of 1 mL of a 3:1 water:DMSO solution of sodium ascorbate (50 mM), dipyridyl ligand (50 mM), and CuSO$_4$ (10 mM) and incubating at room temperature for 2 h with shaking. Removal from the solid-support and deprotection was carried out using standard reagents and protocols recommended by the manufacturer to yield the click lariat RNA6. Following gel purification, we obtained 15 nmol from a 200 nmol synthesis columns corresponding to an isolated yield of 7.5%.

Lariat DNA Synthesis to Test for Loop Size Effect on Branching Efficiency

Following solid-phase synthesis of DNA3-5 precursors, an automated protocol in the Mermade4 instrument was used to yield the lariat DNAs. The synthesis column was treated with 2×200 µl of 3% TCA/DCM for 100 sec. Following the 5'-ODMT deprotection, the column was treated with 5×100 µl of a solution of N,N-diisopropylethylamine (550 µmol), phosphoramidic chloride (160 µmol), and 1-methylimidazole (55.5 µmol) in 5 ml of DCM for 1 min, an additional 5× for 5 min and finally 5× for 15 min. Immediately after the phosphoramidite synthesis, the column was irradiated using a 100 W long-wave UV lamp (365 nm) while flowing ACN in 9×200 µl fractions for 45 min. Immediately following UV deprotection, 0.25 M ETT, the coupling activator, was added to the column in 4×80 µl fractions for 5 min to activate the 5'-phosphoramidite and cyclize the DNA. The 'coupling' was followed by standard capping and oxidation reagents, THF/Py/PAC$_2$O and 10% MeIm in THF for 120 s and 0.02 M I$_2$ in THF/Py/H$_2$O for 80 s respectively. Removal from the solid-support and deprotection was carried out using standard reagents and protocols recommended by the manufacturer to yield the lariat DNAs3-5. MALDI traces indicate that even though the desired lariat DNAs are being synthesized without major inter-molecular side-reactions, there is significant cleavage at 2'-OH site observed (2). Following gel purification we isolated 52.5 nmol, 75 nmol and 16 nmol out of 200 nmol synthesis columns of the respective lariat DNAs3-5 corresponding to isolated yields of 26.3%, 37.5% and 8.1% yield.

Solid-Phase Synthesis of 2'-O-Photoprotected RNA for Lariat ss siRNA Synthesis

Following solid-phase synthesis of RNA7 precursor, the automated protocol in the Mermade4 instrument was used to yield the lariat RNA. The 5'-ODMT deprotection, the phosphoramidite synthesis and the UV deprotection were carried out as before. Immediately following UV deprotection, 0.25 M ETT was added to the column in only 4×60 ul fractions for 5 min to activate the 5'-phosphoramidite and cyclize the RNA. The amount of ETT was reduced in efforts to reduce strand cleavage vs. strand circularization. The capping, oxidation, removal from the solid-support and deprotection were carried out as before to yield the lariat RNA7. Following gel purification, we obtained 64 nmol from a 200 nmol synthesis columns corresponding to a recovered yield of 32%.

Debranching of Lariat and Click Lariat siRNAs

Figure 3C:
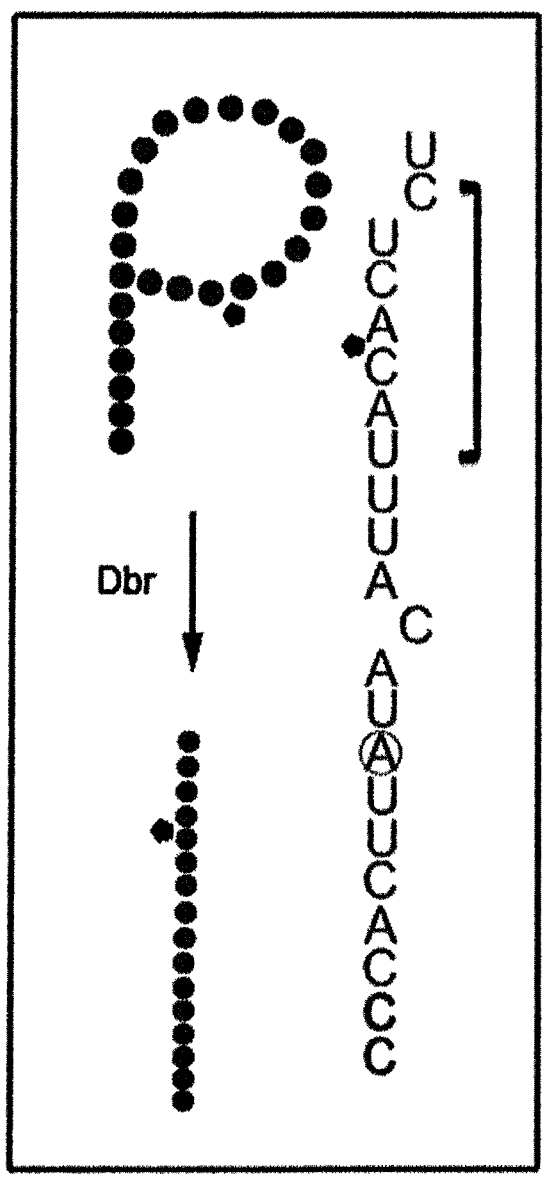
Figure 3E:
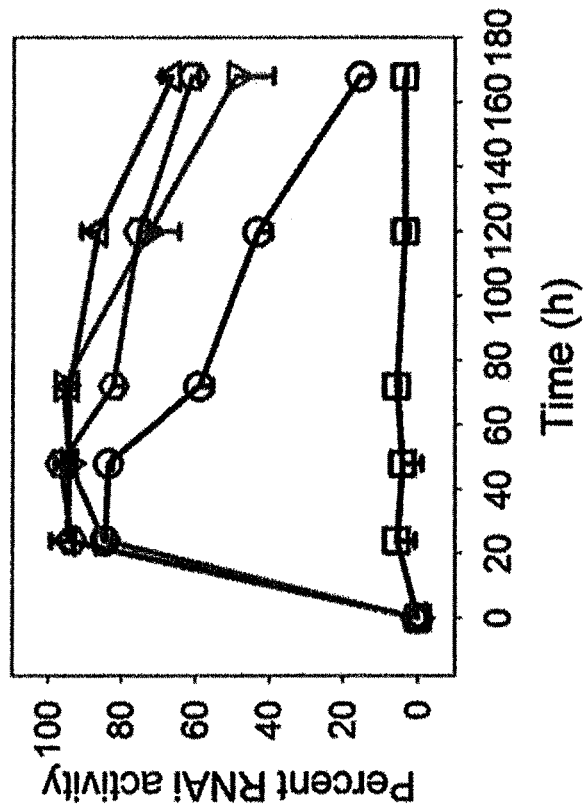
Figure 3D:
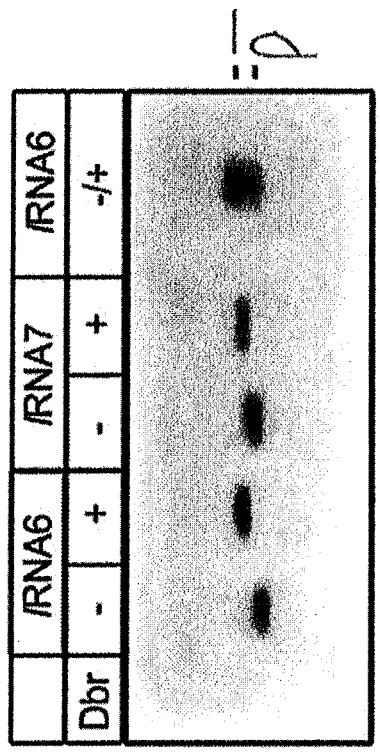

RNA6 or RNA7 (800 pmol) were incubated with Dbr (25 pmol) in a solution of 50 mM Tris.HCl (pH 7.5), MnCl$_2$ (80 nmol), DTT (100 nmol), and NaCl (500 nmol) for 30 min at 30° C. The reaction mixtures were loaded on a 20% PAGE gel (8M Urea) to resolve the debranched RNAs (FIG. 3D).

Plasmid Retransformation and Restriction to Check Gene Integrity

Overnight 500 mL DH5-alpha cultures were inoculated for the CJ22 (50 ng) or pGL3 (50 ng) plasmids containing the Rluc and Fluc genes respectively. Maxi preps (E.Z. DNA Omega) were carried out to recover the amplified plasmids. The recovered plasmids were incubated in 1×NEB Buffers 1 and 4 respectively with 10 U of either BamH1 and Xho1 or Kpn1 and Xho1 at 37° C. for 1 h. The reaction mixtures were loaded on 1% Agarose gel to resolve the restricted fragments that show that the genes of interest are intact after re-transformation (FIG. 12).

Luciferase Assays for RNAi Activity in S2 Cells

S2 cells (100 µl of 200 Kml$^{-1}$) in Schneider's media were plated per well on a 96-well plate. In a sterile tube, 97 µl of media, 1 ul of 40 ng/µl CJ22 plasmid, 1 µl of 20 ng/µl pGL3 plasmid and 1 µl of 30 µM RNA in 1× PBS were combined and vortexed. 6 µl of FuGENE were added to the tube and mixed immediately. After a 10 min incubation, 10 µl of this solution was added per well. Induction of luciferase reporters was achieved by adding 10 µl of 5.5 mM CuSO$_4$ per well 17 h prior to the luciferase assay. Luciferase assays were performed with the Dual Glow Luciferase® system on a Tecan M1000 plate reader. The ratio of Renilla:firefly luciferase activity was measured for each well and normalized to a control well in which no interfering RNA was added but cells were incubated for the same amount of time to control for fluctuations in expression levels over time. The data is presented as % of RNA interference given by the formula: % RNAi=100−((Rh$_{luc}$sample/F$_{luc}$sample)/(R$_{luc}$control/F$_{luc}$control))*100.

Following the synthesis of the large lariat constructs which gave very poor yields, we sought to synthesize smaller lariat siRNAs and use them in RNAi. We chose to lariatize only the active guide strand. As an unmodified single stranded RNA, it would quickly succumb to cellular nucleases. However, the 5'-end of the RNA would be inherently protected by the RNA lariat loop, and we therefore modified the 3'-end 'tail' by incorporating two L-deoxycytosine residues. The use of deoxynucleotides and aryl units to protect the 3'-end overhang of siRNA duplexes is common practice (REF) and we reasoned that L-deoxycytosine residues would further protect the RNA from degradation.

We therefore synthesized RNA6 precursor in the solid-phase with a 5'-azide and 3'-O -propargyl groups as before (FIG. 3B). Given that a splint ligation of such a small RNA construct is not feasible, we chose to carry out the click ligation in the solid-phase in efforts to reduce inter-strand side-reactions (Lewis et al. Discovery and Characterization of Catalysts for Azide-Alkyne Cycloaddition by Fluorescence Quenching. *J. Am. Chem. Soc.* 126: 9152-9153 (2004)). Following the click reaction in the solid phase, removal from the solid support, deprotection, and purification, we could recover RNA6 in 7.5% yield. Given that the synthesis yield of these click-linked siRNA lariats is still not optimal and the synthesis of the branch segment requires reverse amidites, we sought another approach to synthesize these lariat siRNA constructs.

With the 2'-O-photoprotected amidites in hand, we could include a 2'-photoprotected group in a growing RNA strand. We reasoned that if we could generate a 5'-phosphoramidite in the solid-phase by adapting literature reports, following T-unmasking using UV light, we could activate the 5'-phosphoramidite, using ethylthiotetrazole (ETT—a reagent used in amidite coupling), which would then react with the newly unmasked T-OH to yield the 2'-5'-linkage of a native lariat RNA (FIG. 3A).

The possibility of inter-strand coupling prompted us to investigate the effect of the potential loop size (that is the number of nucleotides between the T-photoprotected residue to the 5'-amidite) in both strand circularization and inter-strand side-reactions. Therefore we synthesized DNA3-5 precursors with 2'-NVOM photoprotecting groups and a 5'-ODMT in which the loop size varies from 5, 10 and 15 nts. The 200 nmol solid supports were treated with 3% TCA/DCM to yield a 5'-OH. The synthesis of the 5'-phosphoramidite was carried out by adapting reported conditions. We treated the synthesis columns with a solution of N,N-diisopropylethylamine, phosphoramidic chloride and 1-methylimidazole in DCM to yield the 5'-amidite. Immediately following the amidite synthesis, the column was irradiated with a long wave UV lamp while flowing ACN for 45 min to yield the deprotected 2'-OH. Immediately following the 2'-unmasking, addition of 4×80 µl fractions of ETT activate the phosphoramidite which then reacts with the 2'-OH to yield the native lariat DNA3-5. Following removal from the solid support and deprotection, MALDI traces of the crude products show that although the lariat DNAs are synthesized with no side products from inter-strand reactions observed, some cleavage at the branch-point is occurring due to the presence of a strong peak corresponding to cleavage fragments. Following purification, we could obtain the lariat DNAs in 26.3%, 37.5%, and 8.1% yield respectively.

Undeterred by the low yields of the DNA3 synthesis, we synthesized a RNA7 precursor and carried out a similar set of lariatization reactions in the solid-phase. However we reduced the amount of ETT added in the coupling step as ETT can participate in the base catalyzed cleavage of oligonucleotides which would yield the 3'-segment $dT_{10}$ 'tail' observed in the DNA test oligonucleotides. We therefore added only 4×60 µl of ETT to yield the lariat RNA7. Following removal from the solid support, deprotection, and purification, we could recover RNA7 in 32% yield.

We were curious as to the effect of such small loop sizes on debranching by Dbr. We therefore tested both RNA6,7 in debranching reactions with Dbr and found that both the click-linked lariat and native lariat siRNA are efficiently debranched by Dbr (FIG. 3c). The results suggest that Dbr can debranch smaller lariat structures and that these lariat siRNAs could be useful in RNAi.

Lariat siRNAs for Sustained RNAi Therapy

Based on Ruby et. al. (Intronic microRNA precursors that bypass Drosha Processing. *Nature* 448(7149): 83-86 (2007)), we adapted a dual luciferase assay in which two luciferase genes, firefly and *renilla* luciferases, are transfected into *Drosophila*'s S2 cells. The *renilla* luciferase gene has a miR-1003 target within the 3'-UTR of its mRNA. The location of the miRNA site is important as the RNAi effect observed from target sites at the 3'-UTR are due to siRNA directed mRNA cleavage and degradation, and not processes like translation blockage. We therefore transfected the reporter plasmids into S2 cells with lariat RNA6,7 using a commercially available FuGENE® HD reagent and incubated the cells on a 96-well plate. We used a commercially available Dual Glow Luciferase® system to test for firefly (Fluc) and *renilla* (Rluc) luciferase activity. We normalized percent RNAi activity with the equation, % RNAi=100−(($R_{luc}$sample/$F_{luc}$sample)/($R_{luc}$control/$F_{luc}$control))*100 in which the control well has the reporter plasmids transfected without any additional silencing RNA to account for changes in overall expression levels over time. Surprisingly, lariat siRNAs are not only able to induce RNAi, but they retain ~70% RNAi activity even after 7 days (FIG. 3d). RNA4 (an unmodified single-stranded guide strand) exhibits RNAi activity which peaks at 48 h and quickly drops back to the baseline RNAi activity of the corresponding passenger strand, RNA5. A duplex consisting of RNA4,5 exhibits similar RNAi activity as RNA4 within the 48 h, but ~50% of its effect persists after 7 days following the transfection, long after the RNA4 itself. The click-linked lariat siRNA, RNA6, exhibits strong RNAi activity similar to the siRNA duplex control. Given that the triazole linkage is within the RNA seed region which is known to be intolerant of modifications, this is another powerful example of the biocompatibility of click linkages in the context of RNA function. RNA7 is more efficient than both RNA6 and the siRNA duplex control and ~70% of its effect is still apparent after 7 days.

CONCLUSIONS

Synthesis of lariat RNA constructs on the solid phase through click chemistry and the use of photoprotecting groups is shown to be a viable method for RNAi. The results show that synthetic lariat RNAs, be it click-linked or with native linkages, are efficiently debranched by Dbr and useful for RNAi knockdown of target genes. The triazole linkage within the siRNA guide strand seed region is found to be well tolerated. Lariat siRNAs' retained potency and longer persistence are two attractive qualities sought after in the RNAi literature. This lariat siRNA approach could become easily adaptable and a more potent tool in RNAi-based therapeutics.

The present invention has been described in accordance with several examples, which are intended to be illustrative, rather than limiting, in all aspects. Thus, the present invention is capable of many variations in detailed implementation, which may be derived from the description contained herein by a person of ordinary skill in the art, and should not be limited by the preceding description, but should be construed to be as broad in scope as the following claims.

The invention claimed is:

1. A solid-phase method of preparing an miRNA guide strand precursor having a lariat structure, comprising preparing on a solid support a lariat structure having a miRNA sequence that is at least partially complementary to a target mRNA:
   a. adding at least two nucleotide residues to the solid support in a 3' to 5' direction;
   b. adding residues to the 5' and 2' positions of the 5' terminal residue, producing a 5' strand and a 2' strand;
   c. terminating the 5' strand with a terminal residue having either a 5' alkyne group or a 5' azide group;
   d. terminating the 2' strand with a terminal residue having a 3' terminal alkyne when the terminal residue of the 5' strand has a 5' azide group or a 3' azide group when the terminal residue of the 5' strand has a 5' alkyne group;
   e. ligating the 5' terminal alkyne or azide of the terminal residue of the 5' strand with the 3'-terminal azide or alkyne, respectively, of the terminal residue of the 2' strand to produce a triazole linkage between the terminal residue of the 5' strand and the terminal residue of the 2' strand; and
   f. deprotecting the lariat structure and cleaving the structure from the solid support, wherein the total number of nucleotide residues in the miRNA guide strand precursor is between 20 and 25 residues and has a sequence that is at least partially complementary to an mRNA, thereby producing a miRNA guide strand precursor.

2. The method of claim 1, wherein the terminal residue of the 2' strand is a 2'-3'-dideoxy-3'-O-propargyl-adeno sine residue.

3. The method of claim 1, further comprising protecting the 3' end of the structure from RNAse degradation.

4. The method of claim 1, in which a 2'-deoxyribonucleotide residue is added to the 3' end of the structure to protect the structure from RNAse degradation.

5. The method of claim 1, further comprising incorporating the synthetic nucleic acid lariat in a delivery vehicle.

6. The method of claim 5, in which the delivery vehicle is a liposome.

7. The method of claim 1, wherein the nucleic acid lariat comprises 22 residues.

8. The method of claim 1, wherein the loop portion is between 5and 20 nucleotides in length.

9. The method of claim 8, wherein the loop portion is 15nucleotides in length.

10. A synthetic micro RNA (miRNA) guide strand precursor having a sequence at least partially complementary to an RNA produced by a gene and having a lariat structure, the miRNA guide strand precursor having an oligonucleotide sequence of from 20 to 25 residues and having a 5' end and a 3' end, wherein the 5' end is attached to a 2' position of a residue at least five residues from the 5' end and at least one residue from the 3' end of the oligonucleotide to form a lariat structure comprising a loop portion.

11. The miRNA guide strand precursor of claim 10, in which the loop portion comprising at one 5' to 3' linkage between two residues a triazole linkage.

12. The miRNA guide strand precursor of claim 10, wherein the oligonucleotide comprises ribonucleotide residues.

13. The miRNA guide strand precursor of claim 10, wherein the oligonucleotide is 22 nucleotides in length.

14. The miRNA guide strand precursor of claim 10, wherein the looped portion is between 5 and 20 nucleotides in length.

15. The miRNA guide strand precursor of claim 10, wherein the 3' end of the oligonucleotide is protected.

16. The miRNA guide strand precursor of claim 15, comprising a 2'-deoxyribonucleotide residue at its 3' end.

* * * * *

UNITED STATES PATENT AND TRADEMARK OFFICE
CERTIFICATE OF CORRECTION

PATENT NO. : 9,546,364 B2
APPLICATION NO. : 14/213164
DATED : January 17, 2017
INVENTOR(S) : Subha Ranjan Das et al.

Page 1 of 1

It is certified that error appears in the above-identified patent and that said Letters Patent is hereby corrected as shown below:

In the Claims

Column 25, Line 55, Claim 2, delete "adeno sine" and insert -- adenosine --

Column 26, Line 34, Claim 8, delete "5and" and insert -- 5 and --

Column 26, Line 36, Claim 9, delete "15nucleotides" and insert -- 15 nucleotides --

Signed and Sealed this
Twenty-eighth Day of March, 2017

Michelle K. Lee
*Director of the United States Patent and Trademark Office*